US012588971B2

(12) United States Patent
Pellissard et al.

(10) Patent No.: US 12,588,971 B2
(45) Date of Patent: Mar. 31, 2026

(54) METHOD FOR ANALYZING A DENTAL SITUATION OF A PATIENT

(71) Applicant: DENTAL MONITORING, Paris (FR)

(72) Inventors: Thomas Pellissard, Paris (FR); Guillaume Ghyselinck, Cantin (FR)

(73) Assignee: DENTAL MONITORING, Paris (FR)

( * ) Notice: Subject to any disclaimer, the term of this patent is extended or adjusted under 35 U.S.C. 154(b) by 514 days.

(21) Appl. No.: 18/008,839

(22) PCT Filed: Jun. 9, 2021

(86) PCT No.: PCT/EP2021/065401
§ 371 (c)(1),
(2) Date: Dec. 7, 2022

(87) PCT Pub. No.: WO2021/250065
PCT Pub. Date: Dec. 16, 2021

(65) Prior Publication Data
US 2023/0210633 A1    Jul. 6, 2023

(30) Foreign Application Priority Data
Jun. 9, 2020    (FR) ...................................... 2006015

(51) Int. Cl.
*A61C 7/00*        (2006.01)
*G16H 30/40*       (2018.01)
(52) U.S. Cl.
CPC ............. *A61C 7/002* (2013.01); *G16H 30/40* (2018.01); *G06T 2207/30036* (2013.01)
(58) Field of Classification Search
CPC ....... A61C 7/002; A61C 19/04; A61C 9/0046; G16H 30/40; G16H 10/60; G16H 30/00;
(Continued)

(56) References Cited

U.S. PATENT DOCUMENTS

2003/0101079 A1*  5/2003  McLaughlin ............ A61C 7/00
                                                    705/3
2016/0135925 A1*  5/2016  Mason ................... A61C 7/002
                                                    703/2
(Continued)

FOREIGN PATENT DOCUMENTS

EP          3391810 A1    10/2018
EP          3432217 A1    1/2019
(Continued)

OTHER PUBLICATIONS

International Search Report corresponding to International Application No. PCT/EP2021/065401 dated Aug. 11, 2021, 9 pages.
(Continued)

*Primary Examiner* — Juan M Guillermety
(74) *Attorney, Agent, or Firm* — Ronald M. Kachmarik; Cooper Legal Group LLC

(57)        ABSTRACT

A method for training a neural network intended to analyze a dental situation of an updated patient. A historical learning database is created that relates to a dental body and to a spatial attribute associated with the dental body. The historical learning database includes more than 1,000 historical records, with each historical record relating to a respective historical patient. Each record including a set of historical images all depicting the dental body in the historical patient, called "historical dental body" and an item of spatial information including, for the historical patient, a set of values for the spatial attribute, called "historical spatial information." The neural network is trained, by providing it with the sets of historical images as input and with the historical spatial information as output, with the spatial attribute defining an ordered sequence of variables in a three-dimensional reference frame.

21 Claims, 5 Drawing Sheets

1) analysis according to the invention, at an anterior updated instant 2) analysis according to the invention, at a posterior updated instant 3) comparison of the anterior and posterior spatial information Dynamic information: amount of movement 4) presentation of the results of the comparison

(58) Field of Classification Search
  CPC .......... G16H 50/00; G06T 2207/30036; G06T
        2207/10028; G06T 2207/20081; G06T
      2207/20084; G06T 7/0016; A61B 5/1111;
          A61B 5/7267; G06F 18/214; G06F
          18/24133; G06V 2201/03; G06N 3/08
  See application file for complete search history.

(56)                References Cited

U.S. PATENT DOCUMENTS

| | | | |
|---|---|---|---|
| 2019/0026599 A1* | 1/2019 | Salah | ......................... G06T 7/11 |
| 2020/0066391 A1* | 2/2020 | Sachdeva | ................. A61C 7/10 |
| 2020/0146646 A1* | 5/2020 | Tuzoff | .................. G06T 7/0012 |
| 2021/0082184 A1* | 3/2021 | Claessen | ................... G06T 7/11 |
| 2021/0106403 A1* | 4/2021 | Aptekarev | ............ G06T 7/0014 |

FOREIGN PATENT DOCUMENTS

| | | | |
|---|---|---|---|
| WO | 2016066637 A1 | 5/2016 | |
| WO | 2016066642 A1 | 5/2016 | |

OTHER PUBLICATIONS

Young-Jun Yu, "Machine Learning for Dental Image Analysis",
Nov. 29, 2016, Department of Computer Science, Yonsei Univer-
sity, https://arxiv.org/ftp/arxiv/papers/1611/1611.09958.pdf.
Jie Hu,et al., "Squeeze-and-Excitation Networks", May 16, 2019,
https://arxiv.org/pdf/1709.01507v4.pdf.
Tsung-Yi Lin, et al., "Microsoft COCO: Common Objects in
Context", Feb. 21, 2015, https://arxiv.org/pdf/1405.0312.pdf et https://
arxiv.org/pdf/1703.06870.pdf.

* cited by examiner

[Fig 1]

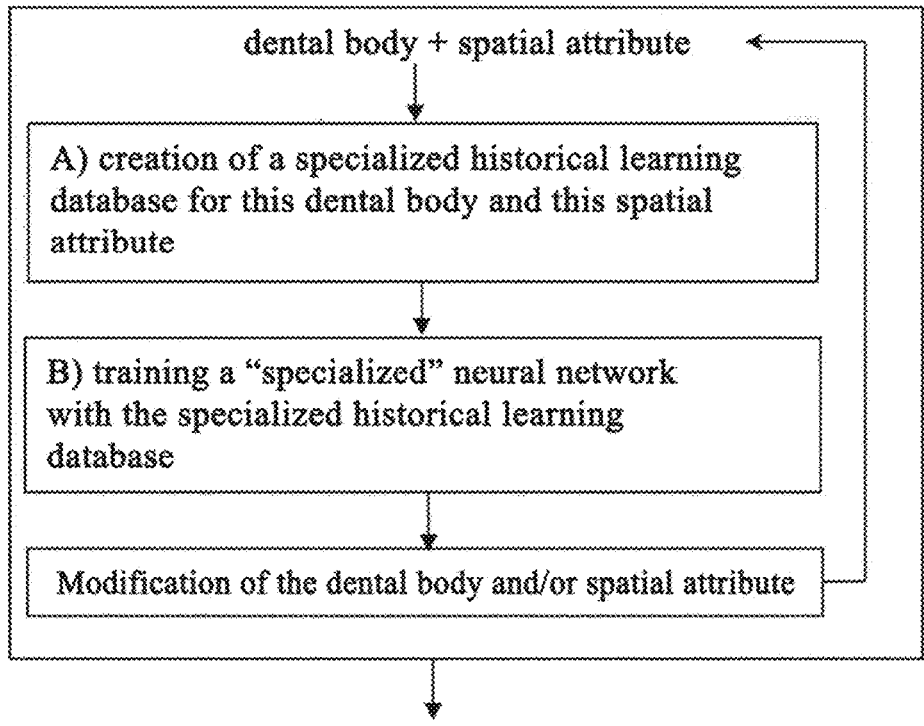

dental body + spatial attribute

A) creation of a specialized historical learning database for this dental body and this spatial attribute B) training a "specialized" neural network with the specialized historical learning database Modification of the dental body and/or spatial attribute Set of specialized neural networks

[Fig 2]

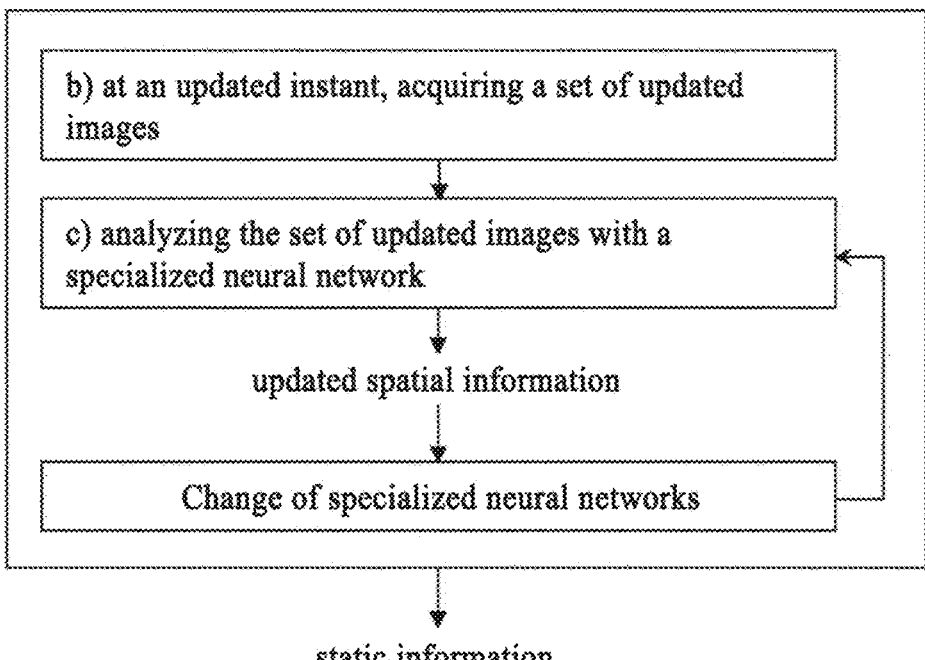

b) at an updated instant, acquiring a set of updated images c) analyzing the set of updated images with a specialized neural network updated spatial information Change of specialized neural networks static information

[Fig 3]

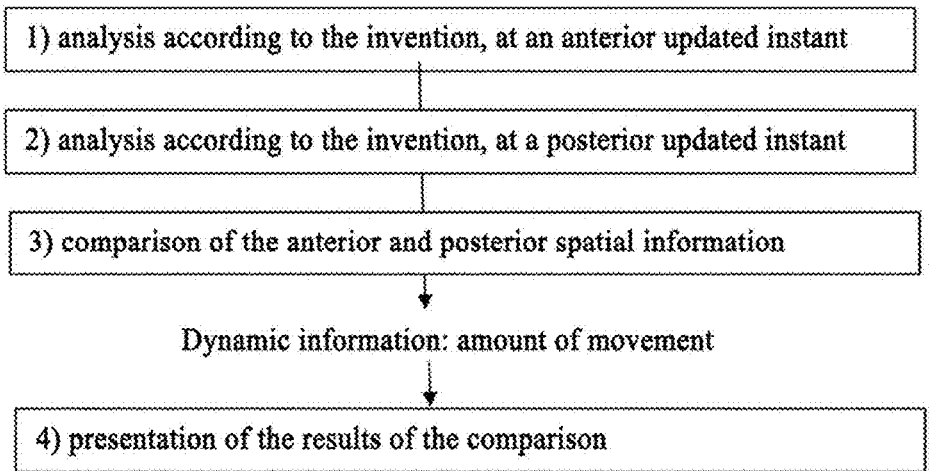

1) analysis according to the invention, at an anterior updated instant 2) analysis according to the invention, at a posterior updated instant 3) comparison of the anterior and posterior spatial information Dynamic information: amount of movement 4) presentation of the results of the comparison

[Fig 4]

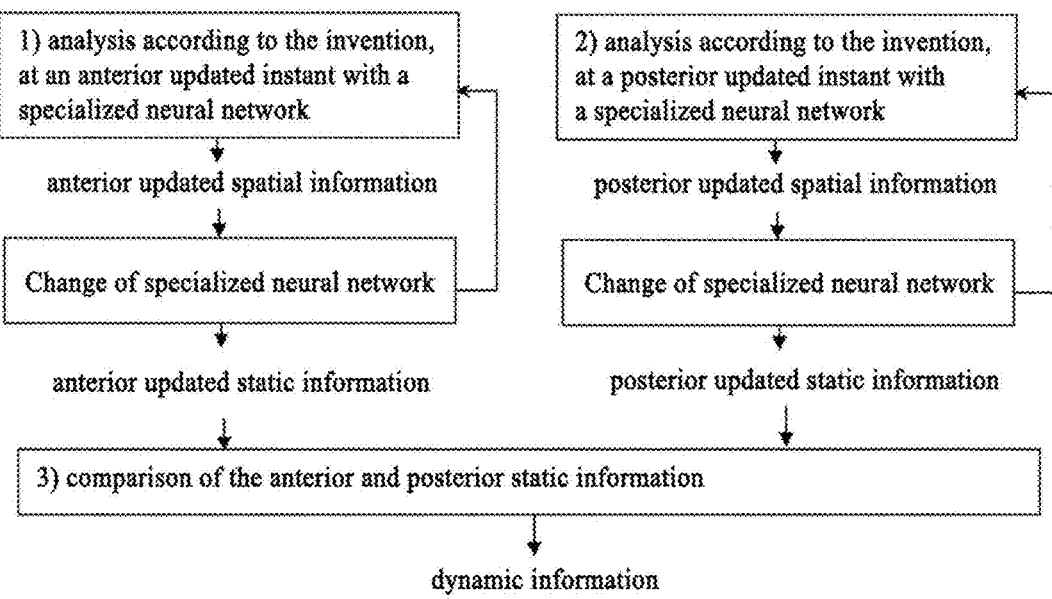

1) analysis according to the invention, at an anterior updated instant with a specialized neural network anterior updated spatial information Change of specialized neural network anterior updated static information 2) analysis according to the invention, at a posterior updated instant with a specialized neural network posterior updated spatial information Change of specialized neural network posterior updated static information 3) comparison of the anterior and posterior static information dynamic information

[Fig 5]
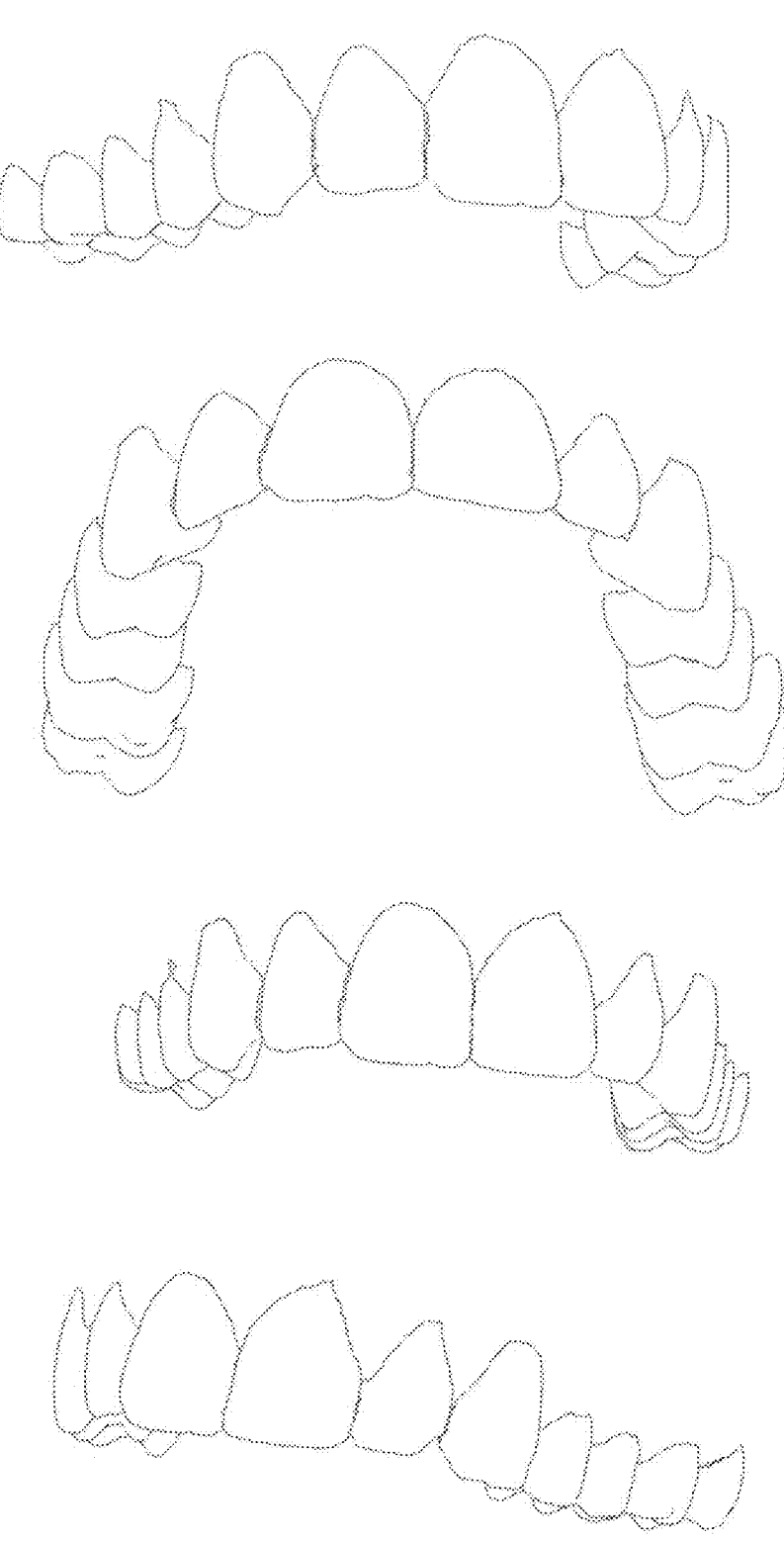

[Fig 6]
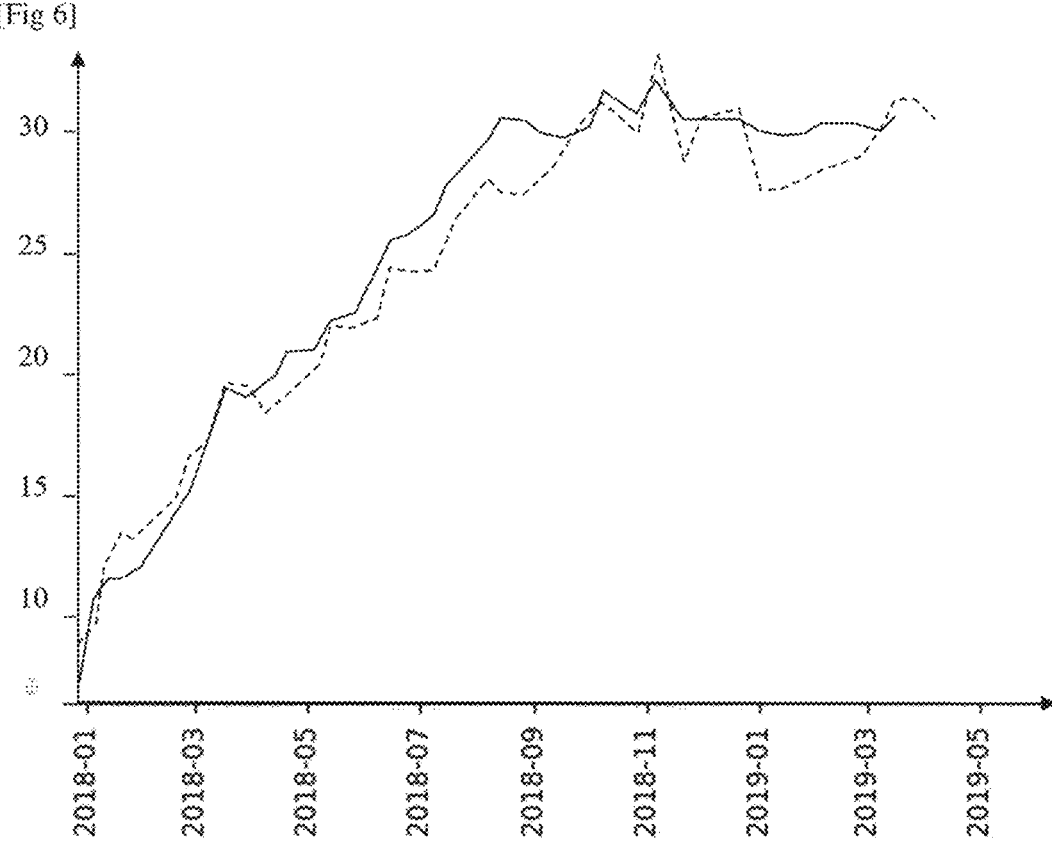
[Fig 7]
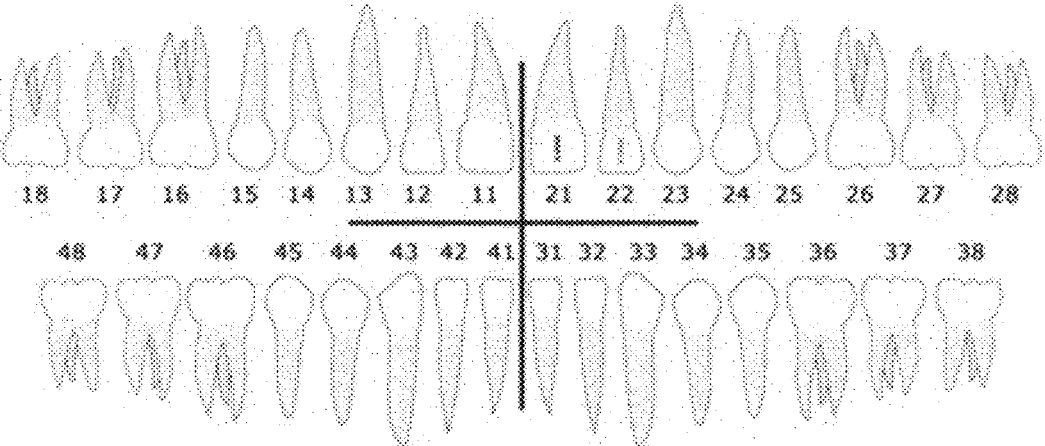

[Fig 8]
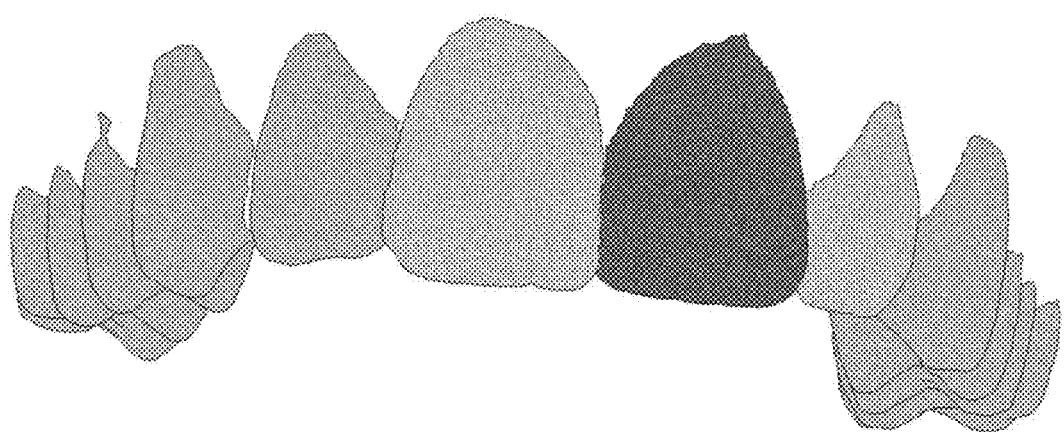

METHOD FOR ANALYZING A DENTAL SITUATION OF A PATIENT

TECHNICAL FIELD

The present invention relates to a method for training a neural network intended to analyze a dental situation of a patient, a method for analyzing a dental situation of a patient implementing the neural network thus trained, and a method for determining an amount of movement of a dental body, in particular for monitoring the activity of an active orthodontic appliance or a loss of effectiveness of a passive orthodontic appliance.

PRIOR ART

The applicant has developed methods for remotely monitoring the dental situation of a patient, before, during or after an orthodontic treatment. These methods rely on comparing photos taken by the patient, at an updated instant, by means of their mobile phone, with views of a three-dimensional digital model of at least one of their dental arcades.

More specifically, an initial model of the dental arcade is created at an initial instant, conventionally with a 3D scanner, and is then divided into tooth models. After the patient has acquired the photos, the initial model is deformed, by moving the tooth models, in order to best match the photos. The comparison of the initial models and of the deformed model thus obtained then provides information relating to the movement of the teeth from the initial instant. Since the initial model is very precise, the same is advantageously the case for the deformed model, and therefore for the information resulting from said comparison.

These methods are particularly described in PCT/EP2015/074868 or PCT/EP2015/074859.

They require significant computation resources, in particular in order to move the tooth models. Typically, several hours of computer processing are required to assess a dental situation.

Moreover, these methods require the creation of the initial model, and therefore the patient traveling to an orthodontist, then the use of a 3D scanner. This procedure expensive and can be unpleasant for the patient.

Therefore, a requirement exists for a method that allows remote monitoring of a patient to be provided and that does not have the aforementioned disadvantages.

An aim of the present invention is to at least partially address these requirements.

SUMMARY OF THE INVENTION

The invention proposes a method for training a neural network intended to analyze a dental situation of an updated patient, said method comprising the following steps:

A) creating a historical learning database relating to a dental body, for example, the number 13 tooth, and to a spatial attribute associated with the dental body, for example, the position of the barycenter of the number 13 tooth;

the historical learning database comprising more than 1,000 historical records, with each historical record relating to a respective historical patient, comprising:

a set of historical images all depicting said dental body in said historical patient "historical dental body"; and an item of spatial information comprising, for the historical patient, a set of values for said spatial attribute, called "historical spatial information", namely, in the considered example, values determining the position of the barycenter of the number 13 tooth for the historical patient;

B) training the neural network, by providing it with said sets of historical images as input and with said historical spatial information as output.

After training, the neural network is thus able to determine an updated item of spatial information for a set of updated images, compatible with the sets of historical images of the historical learning database, and that is entered therein as input.

Preferably, the historical learning database is specialized for a precise dental body and for a spatial attribute with limited variables, which improves its performance capabilities. Preferably, the number of historical images of a historical record is nevertheless limited, which allows the specialized neural network to be subsequently used without having to supply it with many images.

A training method according to the invention preferably has one or more of the following optional feature(s):

the neural network is convolutional (CNN, "Convolutional Neural Network");

the spatial attribute defines:

a position of one or more noteworthy point(s) of the dental body in a three-dimensional reference frame, for example, fixed relative to a dental arcade of the considered patient or relative to a point of a tooth of the considered patient; and/or one or more vector(s) between noteworthy points of the dental body and/or between a noteworthy point of the dental body and another point, in particular a noteworthy point of the considered patient, preferably of the oral cavity of the considered patient;

the dental body is a tooth or a set of less than 5 teeth, preferably less than 4 teeth;

the historical dental body is a tooth having a predetermined number or a set of teeth comprising a tooth having a predetermined number and one or two teeth adjacent to said tooth;

the spatial attribute comprises less than 30, preferably less than 20, preferably less than 10 variables;

the set of historical images of any historical record comprises more than two, preferably more than three, preferably more than 5, preferably more than 6 and/or less than 30, preferably less than 20, preferably less than 15, preferably less than 10 historical images;

each historical image of the set of historical images of any historical record is acquired at an angulation selected from a group of potential angulations, or "standard angulations", comprising more than 2, preferably more than 4, preferably more than 4 and/or less than 30, preferably less than 20, preferably less than 10 potential angulations;

at least three historical images of any set of historical images, preferably all the historical images of any set of historical images, are acquired at different angulations;

the historical images are true color photographs, depicting a dental scene that can be perceived by a human eye, and/or do not depict a dental retractor, and/or are extra-oral;

the historical images are acquired at variable distances from the historical patients, then cropped around the dental body that they depict.

The invention thus relates to a method for analyzing a dental situation of a patient, called "updated patient", at an updated instant, said method comprising the following steps:

a) before the updated instant, training a neural network in accordance with a training method according to the invention;

b) at the updated instant, acquiring, by means of an image acquisition device, a set of updated images compatible with said neural network and depicting said dental body of the updated patient, called "updated dental body";

c) analyzing the set of updated images by means of said neural network so as to obtain an item of spatial information comprising, for the updated patient, a set of values for said spatial attribute, called "updated spatial information".

An image of a dental scene, for example, a photo, is the result of the projection of this dental scene in a plane. The analysis of the depiction, on the image, of a dental body of the dental scene can provide spatial information if the shape of this dental body is known, or if the shape of another object of the dental scene that is depicted and is linked to the dental body is known. Generally, the shape of the dental bodies, and in particular of the teeth, of a patient is not known, however. A simple analysis of an image of a dental scene therefore generally does not allow reliable spatial information to be determined for dental bodies.

According to the principle of die 3D scanner, analyzing several images of the same dental scene can provide precise spatial information concerning a dental body of said dental scene, even if the shape of this dental body was not known. Recognizing the dental body on the images and comparing the images nevertheless requires long and costly operations.

As will be seen in further detail throughout the remainder of the description, and quite unexpectedly, the inventors have discovered that using a neural network allows spatial information to be obtained with very good precision, from simple images, and in particular from photos. In particular, they were surprised to find that the error on the spatial information could be less than 1 mm, 0.5 mm, and even less than 0.3 mm, without having recourse to a three-dimensional model of the dental arcade of the patient. Such precision was actually considered, before the invention, to be impossible to achieve exclusively from images, unless complex processing was carried out, such as with a 3D scanner. In particular, it seemed to be impossible to achieve with simple photos, for example, taken by the patient themselves.

Tests have shown that the updated spatial information is reliable even when the images are photos taken without any particular care with a simple mobile phone, even when the updated patient does not wear a dental retractor and without the mobile phone having to be fixed on a support, for example, a tripod.

Furthermore, while several hours of computer processing until now were required in order to assess each dental situation, a method according to the invention allows an updated item of spatial information to be obtained in a few seconds.

Finally, the updated patient no longer needs to travel to a dental care professional. Therefore, the analysis method can be implemented by any person with a mobile phone, independently of any contact with a dental care professional.

An analysis method according to the invention preferably has one or more of the following optional feature(s):

the image acquisition device is a mobile phone;

the updated images are true color photographs, depicting a dental scene that can be perceived by a human eye;

the updated patient does not wear a dental retractor in step b);

the updated images are extra-oral;

the updated images are acquired at variable distances from the updated patient, then cropped around the dental body that they represent.

Preferably, in step a), a plurality of neural networks is trained with respective historical learning databases that differ in that they relate to different dental bodies and/or different spatial attributes, so as to obtain a plurality of specialized neural networks;

in step b), updated images are acquired and a set of updated images is generated from said updated images for each of said specialized neural networks;

in step c), each of said sets of updated images is analyzed by means of the corresponding specialized neural network, so as to obtain a plurality of updated items of spatial information, which can be generally referred to as static information.

Preferably, each historical learning database relates to a tooth having a number specific to said historical learning database, or a group of teeth, with the numbers of the teeth of said group being specific to said historical learning database.

Preferably, the spatial attribute is the same for all the historical learning databases.

The analysis method thus allows several dental bodies to be analyzed with, for each dental body, a neural network that is specific thereto. The updated spatial information is thus both precise and substantial.

The invention thus unlocks a very broad field of applications.

In a particularly advantageous manner, the analysis method according to the invention can be implemented several times, at different updated instants.

The invention particularly relates to a method for determining an amount of movement between an "anterior" updated instant and a "posterior" updated instant after the anterior updated instant, said method comprising the following steps:

1) implementing an analysis method according to the invention, at the anterior updated instant, so as to obtain an "anterior" updated item of spatial information, or more generally a static "anterior" item of information;

2) implementing an analysis method according to the invention, at the posterior updated instant, so as to obtain a "posterior" updated item of spatial information, or more generally a static "posterior" item of information;

3) comparing the anterior and posterior updated spatial information, or more generally the static anterior and posterior information, so as to obtain an amount of movement between the updated anterior and posterior instants, the comparison can particularly involve finding a difference between the anterior updated spatial information and the posterior updated spatial information (or more generally between the anterior static information and the posterior static information), optionally followed by the division of said difference by the time interval between the anterior and posterior updated instants;

4) preferably, presenting said amount of movement, for example, on a personal computer or a mobile phone screen, preferably to the updated patient and/or to a dental care professional.

A determination method according to the invention preferably has one or more of the following optional feature(s):

the amount of movement defines an amplitude and; or a rate of the movement, by translation and/or by rotation, between the anterior and posterior updated instants, of one or more point(s) of the updated dental body and/or of one or more vector(s) connecting points of the updated dental body or connecting one or more point(s) of the updated dental body and one or more other point(s) of the oral cavity of the updated patient;

in step 3), said amount of movement is compared with a threshold value and, depending on the difference between the amount of movement and the threshold value, the following is determined:

an activity index of an orthodontic appliance worn by the updated patient; and/or an index of conformity of the dental situation of the updated patient with a predefined situation by an orthodontic treatment undertaken by the updated patient, or with a situation resulting from an orthodontic treatment undertaken by the updated patient, or, independently of an orthodontic treatment, with a situation defined by a dental care professional, for example, defined as being normal for the updated patient;

the activity index and/or the conformity index are presented in the form of a graph;

the activity index and/or the conformity index are presented on a screen, for example, on a computer or mobile phone screen.

Preferably, as described above, a plurality of neural networks is specialized for respective teeth or groups of teeth, with each neural network being specialized, for example, for a tooth having a number that is specific thereto.

The determination method according to the invention thus allows an analysis of the evolution over time of several dental bodies with, for each dental body, a neural network that is specific thereto. The amounts of movement are thus both precise and substantial. All these amounts of movement can be generally qualified as dynamic information.

In a preferred embodiment, the specialization is per tooth type. For example, a neural network can be specialized for the canines, another network can be specialized for the incisors, a third neural network can be specialized for the molars, etc.

The specialization can be per tooth number. For example, a neural network can be specialized for number 13 teeth, another network can be specialized for number 14 teeth, a third neural network can be specialized for number 15 teeth, etc.

The analysis and determination methods according to the invention particularly can be used for:

detecting or assessing a position or a shape of a tooth and/or an evolution of a position or a shape of a tooth and/or a rate of evolution of a position or a shape of a tooth, in particular:

during a pre-treatment period, i.e., in a period that precedes an orthodontic treatment;

in the absence of any orthodontic treatment, in particular to monitor the eruption of a tooth or to detect a relapse or an abnormal position of a tooth or to detect an abrasion of a tooth, for example, due to bruxism, or to monitor the opening or closing of a space between two or more than two teeth, in particular between two adjacent teeth, or to monitor the stability or the modification of the occlusion;

in the context of an orthodontic treatment, in particular to monitor the movement of a tooth to a predetermined position, in particular an improved position of the tooth, or to monitor the eruption of a tooth, or to monitor the opening or closing of a space between two or more than two teeth, in particular between two adjacent teeth, for example, in order to create a space suitable for fitting a dental implant; and/or detecting or assessing a position or a shape of an orthodontic appliance, in particular an abnormal position or shape of an orthodontic appliance, for example, the detachment of a ring or an orthodontic aligner, and/or an evolution of a position or a shape of an orthodontic appliance and/or a rate of evolution of a position or a shape of an orthodontic appliance, in particular for:

optimizing the date to snake an appointment with an orthodontist or a dentist; and/or assessing the effectiveness of an active orthodontic treatment; and/or measuring the activity of an active orthodontic appliance; and/or measuring a loss of effectiveness of a passive orthodontic appliance; and/or dentistry; and/or measuring an evolution of the shape of the teeth of the patient between two dates, for example, during pre-treatment, in particular between two dates separated by an event likely to have changed the position and/or the shape of at least one tooth, for example, separated by the occurrence of an impact on the teeth or by the use of a dental device capable of producing an unwanted effect, for example, intended for treating sleep apnea, or by the occurrence of a graft in the mouth of the patient, in particular a periodontal graft, and in particular a gum graft.

Steps A) and B), and/or a) and c), and/or 1) to 3) (excluding step h)), are preferably implemented by a computer. The invention also relates to:

a computer program comprising program code instructions for implementing steps A) and B), and/or a) and c), and/or 1) to 3) (excluding step b));

a computer medium, on which such a program is recorded, for example, a memory or a CD-ROM; and a computer, in which such a program is loaded.

Definitions

The term "patient" is understood to mean any person for which a method according to the invention is implemented, whether or not this person is ill or undergoes an orthodontic treatment.

An "orthodontic treatment" is all or part of a treatment intended to modify the configuration of a dental arcade (active orthodontic treatment) or to maintain the configuration of a dental arcade, in particular following the completion of an active orthodontic treatment (passive orthodontic treatment).

An "orthodontic appliance" is an appliance worn or intended to be worn by a patient. An orthodontic appliance can be intended for therapeutic or prophylactic treatment, but also for aesthetic treatment. An orthodontic appliance particularly can be an arch and braces appliance, or an orthodontic aligner, or an auxiliary apparatus of the Carriere Motion type. Such a aligner extends so as to follow the successive teeth of the arcade on which it is fixed. It defines a generally "U"-shaped channel. The configuration of an orthodontic appliance particularly can be determined to ensure its attachment to the teeth, but also as a function of a desired target position for the teeth. More specifically, the shape is determined in such a way that, in the service position, the orthodontic appliance exerts forces that tend to move the treated teeth toward their target position (active orthodontic appliance), or to hold the teeth in this target position (passive orthodontic appliance, or "retainer").

A "dental situation" defines a set of features relating to a dental arcade of a patient at an instant, for example, the position of the teeth, their shape, the position of an orthodontic appliance, etc., at this instant. These features can also relate to the general shape of the arcade and/or to its arrangement relative to the other dental arcade of the patient, in particular in the "closed mouth" position.

The term "arcade" or "dental arcade" is understood to mean all or part of a dental arcade. The term "image of an arcade" is thus understood to mean a 2-dimensional depiction of all or part of said arcade.

According to the international convention of the International Dental Federation, each tooth of a dental arcade has a predetermined number. The tooth numbers defined by this convention are listed in FIG. 7.

A "scene" is formed by a set of elements that can be observed simultaneously. A "dental scene" is a scene comprising at least one dental body in the oral cavity of a patient.

A "noteworthy point" is a point of a dental scene that can be identified, for example, the apex of the tooth or at the tip of a cusp, an interdental contact point, i.e., of a tooth with an adjacent tooth, for example, a mesial or distal point of the incisal edge of a tooth, or a point at the center of the crown of the tooth, or the "barycenter".

The term "dental body" is understood to mean an element that can be identified in an oral cavity, for example, a tooth, a set of several teeth, for example, a pair or a triplet of adjacent teeth, a gum or a device intended to be supported by a dental arcade, and in particular an orthodontic appliance, a crown, an implant, a bridge, or a facet. The dental body also can be a subset of the aforementioned elements, for example, a tooth having a determined number, or a set of two, three or more than three adjacent teeth, with a tooth of said set having a determined number.

A position of a dental body is "abnormal" when it does not comply with a therapeutic or aesthetic standard.

The term "image" is understood to mean a two-dimensional digital depiction, such as a photograph or an image extracted from a film. An image is made up of pixels.

An "angulation" is an orientation of the optical axis of an image acquisition device relative to a patient, when acquiring an image. By extension, an image "presents" or "has" an angulation or is "associated with" an angulation when it has been acquired at this angulation.

A "tooth zone" of an image is a portion of said image that exclusively depicts a tooth, i.e., which follows the profile of this tooth on this image. In other words, the depiction of said tooth on the image depicts substantially 100% of the tooth zone.

The term "model" is understood to mean a digital three-dimensional model, called "3D" model. A model is made up of a set of voxels. A "tooth model" is a three-dimensional digital model of a single tooth. The term "image of an arcade" or "model of an arcade" is understood to mean a depiction, in two or three dimensions, respectively, of all or part of said arcade.

A 3D scanner, or "scanner", is a well known apparatus for obtaining a model of a tooth or of a dental arcade. It conventionally uses structured light and, on the basis of different images and matching of particular points on these images, is able to form a 3D model.

The methods according to the invention are implemented by a computer, preferably exclusively by a computer, excluding the acquisition of the images. The term "computer" is understood to mean any electronic device, which includes a set of several machines, having computer processing capabilities. The computer can be a server remote from the user, for example, it can be "cloud" based. Preferably, the computer is a mobile phone.

Conventionally, a computer particularly comprises a processor, a memory, a human-machine interface, conventionally comprising a screen, a module for communicating via the internet, via Wi-Fi, via Bluetooth® or via the telephone network. Software configured to implement a method of the invention is loaded into the memory of the computer. The computer also can be connected to a printer.

"First", "second", "updated", historical", "anterior", "posterior" "static", "dynamic" are used for the sake of clarity.

"Anterior" and "posterior" refer to succeeding instants over time.

The "updated" patient is the patient whose dental situation is intended to be assessed. A "historical" patient is a patient with a corresponding historical record.

"Spatial attribute" is a generic term that designates the structure of an item of spatial information. It defines an ordered sequence of variables in a three-dimensional reference frame, for example, an orthonormal reference frame, for example, for a number 14 tooth: (abscissa of the barycenter; ordinate of the barycenter; applicate of the barycenter). The three-dimensional reference frame is determined relative to the considered patient, for example, relative to the center of the oral cavity of the patient. The three-dimensional reference frame is preferably fixed relative to the considered patient or to part of the considered patient. The origin of the reference frame particularly can be the center of the oral cavity.

In particular, the three-dimensional reference frame is independent of the position and the orientation of the image acquisition device when acquiring images.

One or more value(s) of an item of spatial information always can be zero. For example, if the spatial attribute is used to determine the abscissa of a noteworthy point of the dental scene, along the X-axis of the three-dimensional reference frame, only the value of this abscissa is not zero. Alternatively, no value is always zero.

An item of spatial information cannot be deduced solely from the observation of an image, the acquisition conditions of which are not known. In particular, it cannot be deduced solely from the observation of a single acquired image with an image acquisition device for which the orientation and the distance are not known relative to the considered dental body, for example, acquired with a mobile phone that is not fixed on a support, at a predetermined distance from the patient, for example, in abutment on the patient, or with a mobile phone fixed on such a support but for which the orientation can be modified.

As such, an image provides "surface" information, in the plane of the image, for example, the position of a particular point of a tooth depicted on the image in a two-dimensional reference frame of the image. An item of spatial information provides depth information relative to the plane of the image. In the example of the position of a particular point of a tooth depicted on the image, the spatial information provides coordinates of this point allowing it to be positioned not only on the image, but also in the direction of the depth, perpendicular to the plane of the image.

The historical spatial information can be relative, for example, when it represents a distance between two noteworthy points of a tooth or between a noteworthy point of the tooth and a noteworthy point of another tooth, for example, of another adjacent tooth.

An item of spatial information is an occurrence of a spatial attribute. For example, (2; 3; 1.5) can define the position of the barycenter of the number 14 tooth of the patient, “Mr Martin”. It is referred to as “updated” or “historical” according to whether it is associated an updated patient or with a historical patient.

“Anterior” and “posterior” refer to succeeding instants over time.

“Dental body” is a generic term, which designates, for example, the number 14 tooth. “The updated dental body” and the “historical dental body” are occurrences of the dental body in an updated patient and a historical patient, respectively. For example, the number 14 tooth of the patient, “Mr Martin” can be an updated dental body.

“Vertical”, “horizontal”, “right”, “left”, “horizontal” “in front of” or “frontal”, “rear”, “above”, “below”, refer to a patient standing vertically upright.

The information is “static” or “dynamic” according to whether it is the result of an analysis at a single updated instant or whether it is the result of analyses at several successive updated instants.

“Including” or “comprising” or “having” are to be understood in a non-limiting manner, unless otherwise indicated.

BRIEF DESCRIPTION OF THE DRAWINGS

Further features and advantages of the invention will become more clearly apparent upon reading the following detailed description and with reference to the accompanying drawings, in which:

FIG. 1 schematically shows a method in which a method for training a neural network according to the invention is implemented several times in order to obtain a set of neural networks, each specialized on a dental body and/or on an item of spatial information;

FIG. 2 schematically shows a method in which an analysis method according to the invention is implemented several times, each time with a different specialized neural network;

FIG. 3 schematically shows the various steps of a method for determining an amount of movement of an updated dental body;

FIG. 4 schematically shows a method in which a method for determining an amount of movement according to the invention is implemented several times, each time with a different specialized neural network, at two different instants, so as to obtain dynamic information that is both complex and precise;

FIG. 5 is an example of a set of updated images, after processing to isolate the tooth zones;

FIG. 6 is a graph illustrating the precision of an updated item of spatial information obtained according to the invention;

FIG. 7 illustrates the tooth numbering used in the dental field;

FIG. 8 is a graphical representation of a conformity index.

Throughout the various figures, identical reference signs are used to designate similar or identical objects.

DETAILED DESCRIPTION

A training method according to the invention is illustrated in FIG. 1.

Neural Network

In step A), the neural network is preferably specialized for the classification of images.

Preferably, the neural network is a CNN (“Convolutional Neural Network”), preferably selected from among the following neural networks:

AlexNet (2012);
ZF Net (2013);
VGG Net (2014);
GoogleNet (2015);
Microsoft ResNet (2015);
Caffe: BAIR Reference CaffeNet, BAIR AlexNet;
Torch;
VGG_CNN_S, VGG_CNN_M, VGG_CNN_M_2048, VGG_CNN_M_1024, VGG_CNN_M_128, VGG_CNN_F, VGG ILSVRC-2014 16-layer, VGG ILSVRC-2014 19-layer, Network-in-Network (Imagenet & CIFAR-10);
Google: Inception (V3, V4).

Preferably, a “squeeze-and-excitation (SE)” processing block, as described by Jie Hu et al., in “Squeeze-and-Excitation Networks”, arXiv:1709.01507v4 [cs.CV], 16 May 2019, is added to a CNN convolutional operator. More preferably, the neural network is of the VGG type with an SE block.

In order to be operational, the orientation neural network must be conventionally trained using a learning process, called “deep learning”, based on a historical learning database adapted to the desired function.

Historical Learning Database

Training a neural network is a process that is well known to a person skilled inn the art. It involves presenting it with a historical learning database containing historical records each containing an input datum and an output datum.

The neural network thus learns to “match”, i.e., to connect together, the input and output data.

In order to learn to assess, from a set of updated images, an updated item of spatial information relating to an updated dental body depicted on these images, for example, relating to the configuration of the teeth depicted on these images, the historical learning database is preferably made up of a set of historical records each comprising:

- a set of “historical” images all depicting a “historical” dental body of a “historical” patient, preferably a photo depicting at least one tooth of this patient;
- a historical descriptor of the set of historical images, with the descriptor comprising an item of historical spatial information relating to the historical dental body depicted on the historical images.

Preferably, the historical learning database comprises more than 1,000, more than 5,000, preferably more than 10,000, preferably more than 30,000, preferably more than 50,000, preferably more than 100,000 historical records. The higher the number of records, the better the analysis capability of the neural network. The number of historical records is conventionally less than 10,000,000 or 1,000,000.

The historical records are each associated with a respective historical patient.

Historical Images

The sets of historical images all comprise the same number of historical mages, irrespective of the considered historical record. This number is preferably greater than 1, 2, 4, 5 and/or less than 100, 50, 20, 15 or 10, preferably ranging between 5 and 15.

In one embodiment, this number is 3, with the 3 historical images having different angulations.

The historical images are acquired by means of an image acquisition device, preferably selected from among a mobile phone, a “connected” camera, a “smart” watch, a tablet or a personal, fixed or portable computer, comprising an image acquisition system, such as a webcam or a camera.

The historical images are preferably photos, preferably taken with a mobile phone.

Preferably, each historical image is a photograph or is an image extracted from a film. It is preferably in color, preferably in true colors. Preferably, it depicts a dental scene substantially as seen by the operator of the image acquisition device, and in particular with the same colors.

The historical images are preferably extra-oral, i.e., the device for acquiring these images is not introduced into the mouth of the historical patient.

More preferably, the device for acquiring historical images is separated from the mouth of the historical patient by more than 5 cm, more than 8 cm, or even more than 10 cm, which avoids condensation of water vapor on the optic of the image acquisition device and facilitates focusing. Furthermore, preferably, the image acquisition device, in particular the mobile phone, is not provided with any specific optic for acquiring historical images, which is particularly possible due to the separation between the image acquisition device and the mouth of the historical patient during the acquisition.

In one embodiment, the historical patient wears a dental retractor in order to better expose their teeth. The retractor can have the features of conventional retractors. Preferably, it comprises a rim extending around a retractor opening and arranged so that the lips of the historical patient can rest thereon while revealing the teeth of the historical patient through said retractor opening. Preferably, the retractor comprises brackets for separating the cheeks so that the device for acquiring historical images can acquire, through the retractor opening, photos of vestibular surfaces of teeth arranged at the bottom of the oral cavity, such as molars.

In a preferred embodiment, no dental retractor is used. Indeed, tests have shown that the photos taken without a retractor are generally sufficient for implementing the method according to the invention. Of course, if necessary, the historical patient may have to space apart a cheek or a lip with a finger or with a spoon, for example.

All the historical images of a historical record at least partially depict the same dental body of the historical patient associated with the record, for example, the incisors of the historical patient.

A historical image can particularly depict one or more teeth. Preferably, it depicts several teeth and at least part of the gum, or even the lips or the nose of the historical patient.

The historical images of a historical record all depict the same historical dental body, but preferably at different angulations, i.e., they were acquired with different orientations of the image acquisition device relative to the oral cavity of the historical patient. For example, a historical record can comprise 6 historical images depicting the same tooth seen as a "front view", a "right front view", a "right view", a "left front view", a "left view", and a "bottom view", respectively.

The angulations of the historical images of a historical record are preferably substantially identical, irrespective of the considered historical record, for all the historical records relating to the same historical dental body, for example, to the same type of tooth, for example, for all the historical records relating to an incisor, or to the same tooth number, for example, for all the historical records relating to an upper right incisor.

A historical record can comprise one or ore historical image(s) at the same angulation.

When acquiring historical images as well as updated images of a method according to the invention, the angulation can be defined with a level of precision that is not limiting. However, tests have shown that the angulation does not need to be defined very precisely. Advantageously, the acquisition of these images therefore does not require prior training of the operator of the image acquisition device. The historical images, like the updated images, thus can be acquired with minimal care, for example, with a simple mobile phone.

In a preferred embodiment, the angulations are defined very generally. For example, the angulations can be selected from a group of potential angulations made up of the "front view", "right view", "right front view", "left view", "left front view", "bottom view", "front bottom view", "top view", "front top view" of the angulations.

The angulation can be defined relative to a "natural" reference frame, i.e., as a function of the way the patient perceives the image acquisition device. In this reference frame, the angulation is selected, for example, from a group of potential angulations made up of the following angulations:

in the occlusal plane:
"front view" when the optical axis of the image acquisition device is substantially coincident with a straight line at the intersection between the occlusal plane and the median sagittal plane;
"right view" when the optical axis of the image acquisition device is substantially in the occlusal plane and perpendicular to the median sagittal plane, with the image acquisition device being to the right of the patient;
"left view" when the optical axis of the image acquisition device is substantially in the occlusal plane and perpendicular to the median sagittal plane, with the image acquisition device being to the left of the patient;
in the median sagittal plane:
"top view" when the optical axis of the image acquisition device is substantially in the median sagittal plane and perpendicular to the occlusal plane, with the image acquisition device being above the patient;
"bottom view" when the optical axis of the image acquisition device is substantially in the median sagittal plane and perpendicular to the occlusal plane, with the image acquisition device being below the patient.

The angulation can be defined more precisely. In particular, for each of the above angulations, the optical axis of the image acquisition device is in the occlusal plane or the median sagittal plane. It is possible, for example, to add angulations:

in one of the two "front-right" and "front-left" planes inclined at 45° relative to the median sagittal plane and containing the straight line at the intersection between the occlusal plane and the median sagittal plane: front-right and right view, front-right and left view, front-left and right view, and front-left and left view; or
in one of the two "occlusal-top" and "occlusal-bottom" planes inclined at 45° relative to the occlusal plane and containing the straight line at the intersection between the occlusal plane and the plane parallel to the frontal plane and that passes through the center of the oral cavity: occlusal-top and front view; or
in which the optical axis is at the intersection between a first plane selected from among one of the two "front-right" and "front-left" planes and a second plane selected from one of the two "occlusal-top" and "occlusal-bottom" planes.

Preferably, the angulations are selected from group of potential angulations made up of the angulations listed above.

Preferably, the angulations are nevertheless determined as a function of the dental body. For example, if the dental body is a tooth, or a group of teeth, the angulations are preferably fixed as a function of the number of said tooth or of said teeth. The configuration of the mouth does not always actually allow the same angulations to be used for all the teeth.

However, the same angulations can sometimes be used for two different dental bodies, for example, an incisor and a canine.

Precise positioning of the acquisition device when acquiring historical images is not necessary. The historical images thus can be acquired at different distances from the mouth. Tests have shown that the historical dental body, for example, a tooth, can be depicted at a different scale depending on the considered historical image and/or depending on the considered historical record, without the performance capabilities of the trained neural network being substantially affected in a significant manner.

Preferably, however, the image acquisition device is fixed on a support that s placed in abutment on the body of the historical patient, preferably introduced into the mouth of the historical patient. When the support is rigid, it advantageously imposes a predetermined distance between the image acquisition device and the mouth of the historical patient. The performance capabilities of the neural network are thereby improved.

Preferably, the support supports a conventional dental retractor. Such a dental retractor conventionally comprises a rim extending around a retractor opening and arranged so that the lips of the historical patient can rest thereon while revealing the teeth of the patient through said retractor opening.

Preferably, an image capture device is used as described in the European patent application filed on 10 Oct. 2017 under No. 17 306 361.1.

Furthermore, preferably, the historical images are cropped before being incorporated into a historical record. "Cropping", or "re-cutting", is a conventional operation that includes trimming an image in order to isolate the relevant part therefrom, then normalizing the dimensions. Preferably, the historical images are trimmed in order to isolate the historical dental body, i.e., to substantially only depict the historical dental body. Re-cutting can be carried out manually or, as described hereafter, by a computer, and in particular by means of a neural network trained to this end. Re-cutting the historical images considerably improves the performance capabilities of the trained neural networks.

Tests have also shown that, as indicated above, no angulation needs to be precisely set.

Historical Dental Body and Specialization

The denial body particularly can be a tooth or a set of teeth or a dental arcade. Preferably, it is selected so as to limit the variety of its shape between the various historical records. The dental body preferably is a particular type of tooth, or a tooth having a particular number.

A "historical" dental body is the dental body in the particular case of a considered historical patient. In other words, in the historical learning database, all the historical dental bodies are particular occurrences of the dental body associated with the learning database.

Preferably, the learning database, and therefore the neural network, are specialized only for the teeth with a particular number. For example, they are specialized for the upper right incisors. All the historical images of a historical record then all depict the same historical tooth, the historical spatial information of this historical record relates to this historical tooth, and all the historical teeth of the learning database use the same number. This specialization of the neural network for a tooth number considerably improves its efficiency.

Several neural networks specialized in this way are preferably trained, with each neural network being trained with a historical learning database dedicated to a tooth type or to a tooth number. Advantageously, the analysis of a dental situation can thus implement, for each tooth of the updated patient, a specialized neural network for the corresponding tooth type or number.

Historical Description

A historical description of a set of historical images comprises an item of historical spatial information, i.e., a set of values for the variables of a spatial attribute, with these values relating to the historical dental body depicted on the historical images. By definition, a spatial attribute comprises at least three variables corresponding to the three dimensions of the space. The spatial information is therefore a set of at least three values for at least three respective variables of the spatial attribute.

The spatial attribute is the same for all the historical images of the set, but also for all the historical records.

It can particularly define:

one or more position(s) in space of one or more dental bodies and; or of one or more dental body part(s); and/or one or more orientation direction(s) in space of one or more dental bodies and/or of one or more parts of a dental body; and/or one or more orientation courses in space of one or more dental bodies and/or of one or more dental body part(s).

Said part of the dental body can be, for example:

one or more point(s), for example, if the dental body is a tooth, a contact point with an adjacent tooth or the barycenter of the tooth; and/or one or more row(s), for example, if the dental body is a tooth, a separation row between an adjacent tooth or an edge of a cusp of the tooth; and/or one or more surface(s) of this dental body.

In particular, if the spatial attribute $(x_A, y_A, z_A, x_B, y_B$ and $z_B)$ defines positions for two points $(x_A, y_A$ and $z_A)$ and $(x_B, y_B$ and $z_B)$, respectively, in an ordered manner (with the position of the point being A before the position of point B), it indirectly defines an orientation direction, an orientation course and a distance. If it defines positions for three points and these positions are ordered, it indirectly defines three orientation directions, and therefore an angle between pairs of these directions, an orientation course along each of these directions, and three distances.

For example, if it defines the position of the barycenter a first tooth, then the position of the barycenter of the adjacent tooth, to the left of the first tooth, the spatial attribute directly defines the position of these barycenters, but also, indirectly defines the orientation direction of the straight line that connects these points, an orientation course, from the first barycenter to the second barycenter, and a distance between these barycenters.

A spatial attribute can define an absolute position, in a three-dimensional reference frame that is fixed relative to the patient, for example, the origin of which is at the center of the oral cavity of the considered patient, the abscissa axis is horizontal and oriented toward the front, the ordinate axis is horizontal and oriented toward the right and the applicate axis is vertical and oriented upward. It can also define a vector between two points, i.e., a relative position of one point relative to another one point. For example, the spatial attribute can be $(x_B-x_A, y_B-y_A, z_B-z_A)$, i.e., provide the position of point B relative to point A.

The spatial information can thus define an absolute or relative position, and/or an orientation direction and/or an orientation course and/or a distance in a particular dental situation.

Determining the historical spatial information of a historical record does not pose any problems. It can be determined by any means, for example, manually or by a computer, in particular by taking measurements from the historical patient or from a plaster cast of their teeth or from a digital three-dimensional model of the dental arcade supporting the considered tooth.

Preferably, the spatial attribute defines less than 30, preferably less than 20, preferably less than 10 variables, preferably less than 5 variables, preferably less than 4 variables. The effectiveness of the trained neural network is improved.

In one embodiment, the spatial attribute defines positions in space for 1, preferably more titan 1, preferably more than 2 and/or less than 5, preferably less than 4, noteworthy points of the dental body, preferably a tooth with a particular number. Limiting the historical spatial information relating to a tooth to a limited number of points considerably improves the efficiency of the neural network.

In step B), the neural network is trained with the historical learning database, by successively presenting it with the historical records, and, more specifically, the sets of historical images as input and the historical spatial information as output.

It thus learns to provide, as output, from a set of images similar to a set of historical images presented thereto as input, a corresponding item of spatial information. In particular, after having been trained thus, the neural network can provide "updated" spatial information relating to an "updated" dental body of an "updated" patient, at an "updated" instant. The updated spatial information therefore can be used, alone or combined with other information, to analyze a dental situation of the updated patient. An analysis method according to the invention comprises steps a) to c), as illustrated in FIG. 2.

The neural network trained thus is thus able to determine an updated item of spatial information for a set of updated images, compatible with the sets of historical images of the historical learning database, taken on any updated patient, and that is presented thereto as input.

Step a) involves executing steps A) and B) above.

In step b), a set of updated images depicting the updated dental body, preferably an updated tooth, of the updated patient is acquired at the updated instant by means of an image acquisition device.

The updated instant can be:

independent of any orthodontic treatment, for example, so that each patient can monitor their dental situation at any instant, with their mobile phone;

during an active orthodontic treatment;

after an active orthodontic treatment, in particular during a passive orthodontic treatment.

The analysis method particularly can be implemented during an active orthodontic treatment in order to monitor the progress thereof, with the updated instant preferably being less than 3 months, less than 2 months, and/or more than 1 week, preferably more than 2 weeks, after fitting an active orthodontic appliance, for example, an orthodontic aligner (or "aligner") or an orthodontic arch, intended to correct the position of the teeth of the updated patient.

The analysis method also can be implemented after an orthodontic treatment, in order to check that the position of the teeth does not evolve unfavorably ("relapse"). The updated instant is then preferably less than 3 months, less than 2 months, and/or more than 1 week, preferably more than 2 weeks after the completion of the active orthodontic treatment and the fitting of a passive orthodontic appliance intended to hold the teeth in position, called "retainer".

The updated images are preferably extra-oral.

Preferably, the updated images are photographs or images extracted from a film. They are preferably in color, preferably in true colors. Preferably, they depict the dental arcade substantially as seen by the operator of the image acquisition device.

In one embodiment, the updated patient wears a dental retractor in order to better expose their teeth. Preferably, however, no dental retractor is used. Of course, if necessary, the updated patient may have to space apart a cheek or a lip with a finger or with a spoon, or with any other utensil suitable for this purpose, for example.

An updated image can depict one or more teeth. Preferably, it depicts at least part of the gum, or even the lips or the nose of the patient.

All the updated images must be adapted to the neural network, i.e., compatible therewith. In other words, all the updated images must be such that it could have been used for a historical record.

The number of updated images is preferably identical to the number of historical images of a historical record.

The updated images must depict the same dental body as the historical images, for example, the number 14 tooth.

The angulations of the updated images are preferably similar or close to those of the historical images of any historical record.

In general, the updated images must be similar to the historical images used for training the neural network. For example, if these historical images are extra-oral photos that have generally been taken by the historical patients themselves, at a variable distance, for example, at a distance ranging between 10 and 50 cm from their mouths, with an approximate angulation (for example, as a "front view" or as a "right view"), then preferably the updated images are also photos taken under these acquisition conditions. If the historical images depict views taken with a dental retractor, it is preferably the same for the updated images.

The updated images are acquired by means of an image acquisition device, which can be identical or different, preferably of the same type as that used for acquiring historical images.

It is preferably selected from among a mobile phone, a "connected" camera, a "smart" watch, a tablet or a personal, fixed or portable computer, comprising an image acquisition system, such as a webcam or a camera. Preferably, the image acquisition device is a mobile phone. Preferably, the image acquisition device, in particular the mobile phone, is not provided with any specific optic for acquiring updated images.

More preferably, in order to acquire an updated image, the device for acquiring updated images is separated from the mouth of the updated patient by more than 5 cm, more than 8 cm, or even more than 10 cm and/or less than 50 cm. Advantageously, this distance does not need to be set precisely.

Preferably, however, like the historical images, the updated images are "cropped" (or "re-cut") before being incorporated into the set of updated images that will be entered into the neural network trained with the historical learning database. Preferably, the updated images are trimmed in order to isolate the updated dental body, i.e., to substantially depict only the updated dental body. Re-cutting can be carried out manually or, preferably by a computer, and in particular by means of a neural network trained to this end.

In particular, a neural network can be trained to identify the dental body on images, for example, to identify the tooth zones. Such a neural network for "identifying dental bodies" is described hereafter. In order to crop an updated image, the updated dental body simply needs to be identified with this neural network, the smallest rectangle that can contain the dental body identified on this image needs to be defined, so as to retain only the inside of this rectangle in order to define a cut, and then the dimensions of the cut need to be normalized in order to define the updated image to be incorporated into the set of updated images. If the length: width ratio of the rectangle is substantially always the same, irrespective of the updated image, it is likely that the conditions for acquiring the images are similar, which is advantageous. Normalizing the dimensions of the cut involves adjusting these dimensions so that all the updated images have the same dimensions. Preferably, the operation of re-cutting the historical images is similar to that of the updated images, so that the dimensions and the number of pixels of these images are similar or substantially identical.

Re-cutting the historical images and the updated images considerably improves the performance capabilities of the trained neural networks.

The image acquisition device is used by an operator, who is preferably the updated patient or a close associate of the updated patient, but this can be any other person, in particular a dentist or an orthodontist or a caregiver. Preferably, the updated images are acquired by the updated patient.

Preferably, the updated images are acquired without using a support, bearing on the ground and immobilizing the image acquisition device, and in particular without a tripod.

In one embodiment, however, the image acquisition device is attached to a support that is positioned in abutment on the body of the historical patient, preferably partially introduced into the mouth of the historical patient. When the support is rigid, it advantageously imposes a predetermined distance between the image acquisition device and the mouth of the updated patient. The performance capabilities of the neural network are thereby improved.

Preferably, the support supports a conventional dental retractor. Such a dental retractor conventionally comprises a rim extending around a retractor opening and arranged so that the lips of the updated patient can rest thereon while revealing the teeth of the updated patient through said retractor opening.

Preferably, an image capture device is used as described in the European patent application filed on 10 Oct. 2017 under No. 17 306 361.1.

Constitution of the Set of Updated Images During Acquisition

More preferably, the operator is guided, during step b), preferably in real time, to orient the image acquisition device at predetermined angulations, and/or, preferably, to take predetermined number of images at the various angulations, and/or to orient the image acquisition device at the required angulations.

To this end, an application is preferably loaded into the image acquisition device in order to provide onboard control during step b), i.e., to check that the number and/or the angulation and/or the quality of the updated images are satisfactory.

The application can particularly implement fool-proofing means facilitating the approximate positioning of the image acquisition device relative to the updated patient before acquiring the updated image.

The fool-proofing means can particularly comprise a reference that appears on the screen of the image acquisition device and that the operator must match, for example, superimpose, with a portion of the updated patient displayed on this screen, for example, a profile of a tooth, a gum, a lip, or of the face.

The reference can be, for example, a geometric shape, for example, a point, one or more lines, for example, parallel lines, a star, a circle, an oval, a regular polygon, in particular a square, a rectangle or a diamond, or any combination of one or more of these shape(s). The one or more reference(s) is/are preferably "fixed" on the screen, i.e., they do not move on the screen when the image acquisition device is in motion.

The reference can comprise, for example, a horizontal line intended to be aligned with the general direction of the depiction, on the screen, of the horizontal joint between the upper teeth and the lower teeth when the teeth are clamped together by the updated patient, and/or a vertical line intended to be aligned with the depiction of the vertical joint between the two upper incisors. A reference can be formed, for example, by two circles to be placed above the depiction, on the screen, of the two eyes of the updated patient. A reference can be formed, for example, by an oval to be placed around the depiction, on the screen, of the mouth or of the face of the updated patient.

The "portion of the patient" also can be on a support worn by the updated patient, for example, supported by a dental retractor or by a part bittern by the updated patient.

The application can also help the operator to modify the angulation of the image acquisition device, for example, by announcing or displaying messages on the screen, such as, for example, "take a right photo", "higher", "lower", etc., or by emitting a series of beeps, the frequency of which increases as the orientation of the image acquisition device improves. To this end, it must analyze the image displayed on the screen of the image acquisition device in real time, in particular to determine whether the dental body is depicted and, preferably, to check whether the angulation is suitable.

The algorithms for detecting objects in images are well known to a person skilled in the art and can be used to search for the dental body in the displayed image. Preferably, a neural network is used for identifying dental bodies, preferably selected from among "Object Detection Networks", for example:

R-CNN (2013);

SSD (Single Shot MultiBox Detector: Object Detection Network), Faster R-CNN (Faster Region-based Convolutional Network method: Object Detection Network);

Faster R-CNN (2015);

SSD (2015);

RCF (Richer Convolutional Features for Edge Detection) (2017).

Training a neural network for detecting a dental body, for example, a tooth with a determined number, in an image poses no problem to a person skilled in the art. In particular, the neural network is provided with images as input and information is provided as output relating to the presence or absence of the dental body.

The following articles particularly deal with detection or segmentation: https://arxiv.org/pdf/1405.0312.pdf et https://arxiv.org/pdf/1703.06870.pdf.

In one embodiment, said neural network is trained with a learning database made up of a set of more than 1,000, preferably more than 10,000 records, each comprising:

an image comprising a zone depicting the dental body, for example, comprising at least one tooth zone relating to a tooth with a determined number;

a description of said image identifying the zone depicting the dental body on said image.

During training, the neural network is supplied with each image as input, while the associated descriptor is supplied as output from the neural network.

On completion of said training, the neural network is thus able to determine a zone depicting the dental body, for example, a tooth zone, in an image that is supplied thereto as input.

FIG. 5 represents a set of updated images, taken at different angulations, after processing with a neural network thus trained.

The angulation also can be identified by a neural network trained to this end. The neural network is preferably selected from among CNNs, with the last layer of the neural network operating a regression.

Said neural network is trained with a learning database made up of a set of more than 1,000, preferably more than 10,000 records, each comprising:

an image comprising a zone depicting the dental body, for example, comprising at least one tooth zone relating to a tooth with a determined number;

a descriptor of said image identifying the angulation of said image.

During training, the neural network is supplied with each image as input, while the associated descriptor is supplied as output from the neural network.

On completion of said training, the neural network is thus able to determine the angulation of an image that is supplied thereto as input.

Preferably, the application defines a set of predetermined angulations and, for each predetermined angulation, a number of updated images to be acquired. When the application is activated, in step b), it preferably implements the following steps, in real time:

at a current instant, analyzing the image displayed on the screen of the image acquisition device, or "current image", so as to determine whether the dental body is depicted, and preferably the angulation of the image acquisition device, or "current angulation";

if the dental body is depicted and, preferably if the current angulation complies with the current requirement, i.e., if it is still necessary, at the current instant, to acquire an updated image with the current angulation, triggering said acquisition by the operator or automatically;

otherwise, preferably, notifying the operator so that they modify the angulation of the image acquisition device or, if an additional updated image no longer needs to be acquired, so that it ends in step b).

In a preferred embodiment, the acquisition s triggered automatically, i.e., without the action of an operator, as soon as the displayed image depicts the dental body and that the angulation is approved by the image acquisition device.

In order to guide the operator, written and/or voice messages can be issued by the image acquisition device. For example, the image acquisition device can announce "take a front photo", issue a signal to notify the operator that the orientation is acceptable or, on the contrary, that they need to retake a photo.

The end of the acquisition process can be announced by the image acquisition device orally or by a display on the screen.

Guiding the operator when acquiring updated images advantageously allows a set of updated images to be formed that are immediately suitable for the trained neural network.

Constitution of the Set of Updated Images after Acquisition

The set of updated images also can be partially or totally formed after acquiring the updated images, by selecting a sufficient number of updated images that depict the updated dental body at desired angulations.

Determining whether an updated image can belong to a set of updated images specialized for an updated dental body, for example, a tooth number, involves ascertaining whether this updated image depicts this updated dental body, for example, a tooth with this number, and, preferably, checking that the angulation is suitable.

The selection can be manual, in particular when the desired angulations are rough. It is easy, for example, to take a front view photo, a right view open mouth photo, a left view open mouth photo, a right view closed mouth photo, and a left view closed mouth photo.

The updated images also can be selected by a computer. Neural networks such as those described above for acquiring images can be used. The identification of a dental body and/or the determination of the angulation also can be carried out using a conventional analysis of the image, but such an analysis is slow.

If the updated image depicts the dental body with an angulation and the set of updated images still requires an additional updated image for this angulation, the updated image is added to said set.

If the updated image depicts the dental body with a desired angulation, but it is superfluous, it can replace another updated image present in the specialized set if it is of higher quality, for example, since it depicts more surface area of the dental body than said other updated image.

In step c), the set of updated images formed in step b) is entered into the neural network trained in step a).

The neural network in response provides updated spatial information relating to the updated dental body.

Multiple Execution with Different Neural Networks

The neural network is preferably specialized for a limited dental body, for example, a tooth with a determined number, and the spatial attribute preferably comprises a limited number of variables. Preferably, the analysis method is then executed several times at the updated instant, by modifying the considered dental body and/or the considered spatial attribute each e.

All the updated spatial information thus determined is called "static information". It allows a detailed analysis to be obtained of the dental situation of the updated patient, by multiplying the recourse to specialized neural networks.

In a preferred embodiment, in step a), several specialized neural networks are trained, with each neural network being specialized for a dental body, preferably specialized for a respective tooth type or tooth number. Preferably, in step b), a number of updated images is then acquired that is sufficient to form sets of "specialized" updated images that are suitable for each of the specialized neural networks.

Preferably, the updated images are all acquired substantially simultaneously. If necessary, the batch of acquired updated images is analyzed in order to identify the one or more specialized set(s) to which they can belong.

The static information can be enhanced. For example, for each one of a triplet of adjacent teeth made up of a central tooth, a left tooth and a right tooth, with the central tooth being between the left and right teeth, the analysis method can be implemented to determine the position of the barycenter of the tooth in a reference frame that is fixed relative to the dental arcade supporting these teeth. The set of these three positions is static information. In order to enhance this static information, it is possible to determine, from the three positions, an angle formed by two straight segments having the barycenter of the central tooth as the common origin and respectively passing through the barycenters of the left and right teeth. The distances between the barycenter of the central tooth, on the one hand, and the barycenter of the left tooth or the barycenter of the right tooth, on the other hand, also can be determined.

The analysis method can be executed several times, by modifying the considered spatial attribute each time. For example, the analysis method can be implemented to determine the position of the contact point of a tooth with a first adjacent tooth, then to determine the position of the contact point of the tooth with a second adjacent tooth. The set of coordinates defining these two positions is static information.

The analysis method is preferably executed several times, by modifying the considered dental body or the considered spatial attribute each time. If, for example, a triplet of adjacent teeth is considered that is made up of a central tooth, a left tooth and a right tooth, with the central tooth being between the left and right teeth, the analysis method can be successively implemented in order to determine, in a fixed reference frame relative to the dental arcade supporting these teeth, the position of the barycenter of the left tooth, then the position of the barycenter of the right tooth, then to determine the position of the contact point of the central tooth with the left tooth, then the position of the contact point of the central tooth with the right tooth.

In order to enhance the static information obtained thus, an angle can be measured, for example, between two planes perpendicular to a straight line connecting the two barycenters of the right and left teeth, and to a straight line connecting the two contact points of the central tooth with the left and right teeth, respectively. This angle thus provides information relating to the orientation of the central tooth relative to the right and left teeth.

Use of the Static Information

The static information can be used to assess the dental situation of the updated patient.

It particularly can be used to assess whether an updated dental body is in a position that belongs to a region of the predetermined space, and in particular to a region defining a set of predefined positions, for example, that are considered to be acceptable. For example, such a region can be defined around a tooth, or a noteworthy point of a tooth, so that if the tooth even partially leaves this region, or if the noteworthy point leaves this region, the dental situation is considered to be abnormal. Such a region also can be defined around an orthodontic appliance, or a noteworthy point of an orthodontic appliance, so that if the orthodontic appliance even partially leaves this region, or if the noteworthy point leaves this region, the dental situation is considered to be abnormal.

The static information can be used to assess whether an updated dental body has an orientation that belongs to a set of predetermined orientations, and in particular to a set of orientations defining a set of orientations considered to be acceptable. The orientation of a tooth particularly can be defined by the angle formed by two straight lines passing through a noteworthy point of the tooth, for example, its barycenter, with the first of said straight lines passing through a noteworthy point, for example, the barycenter, of a tooth to the right of the tooth, preferably adjacent to the tooth, and the second of said straight lines passing through a noteworthy point, for example, the barycenter, of a tooth to the left of the tooth, preferably adjacent to the tooth.

The static information also can be used to assess whether a distance between a noteworthy point of an updated dental body and another noteworthy point of the dental arcade supporting said updated dental body, for example, if the distance between the barycenter of a tooth and the barycenter of a tooth adjacent to the tooth, belongs to a predetermined range of distances, and in particular to a set of distances considered to be acceptable.

The limits of the regions or ranges of acceptability defined for an item of static information, or "static constraints", are preferably defined by a dental care professional.

The static information particularly can be used to determine whether the dental situation of the updated patient has become abnormal. For example, in order to detect relapse, the static constraints can correspond to the dental situation on completion of the orthodontic treatment, with an optional tolerance margin.

The static information can be used to determine the position of a first dental arcade of the updated patient relative to the second dental arcade of the updated patient, in particular to detect and/or assess the presence of a vertical or horizontal overhang, in particular when said overhang is abnormal.

For monitoring an orthodontic treatment, the static constraints can correspond to the dental situation that is expected at the updated instant or on completion of the orthodontic treatment, with an optional tolerance margin.

In the absence of any treatment, the static constraints can define a set of dental situations that are considered to be normal.

In one embodiment, the static constraints are independent of the updated patient, i.e., applicable to any patient of a group of patients. They thus form a standard, or "standard set-up".

Preferably, the standard is specific to a pathology and/or to a type of orthodontic treatment, and/or to a group of patients sharing a common characteristic, for example, belonging to the same age class and/or the same gender. The standard can particularly determine an arcade shape.

The standard can particularly define a dental situation on completion of a treatment or at the updated instant.

A message can be sent to the updated patient and/or to a dental care professional in order to notify them, particularly when a static constraint is not respected, for example, if a position, an orientation and/or a distance determined from the static information is not (or are not) acceptable.

The static information can be presented in the form of a graph.

For example, the static information can be presented on a computer screen or a mobile phone screen.

For example, the graph can represent teeth with a color that depends on a conformity index expressing the conformity of the position of each tooth with a predefined position, for example, with a predefined position at the updated instant. For example, the darker the tooth, the further away its position from the predefined position.

The static information particularly can be used for:

detecting or assessing a position or a shape of a tooth and/or an evolution of a position or a shape of a tooth and/or a rate of evolution of a position or a shape of a tooth, in particular:

during a pre-treatment period, i.e., in a period that precedes an orthodontic treatment;

in the absence of any orthodontic treatment, in particular to monitor the eruption of a tooth or to detect a relapse or an abnormal position of a tooth or to detect an abrasion of a tooth, for example, due to bruxism, or to monitor the opening or closing of a space between two or more than two teeth, in particular between two adjacent teeth, or to monitor the stability or the modification of the occlusion;

in the context of an orthodontic treatment, in particular to monitor the movement of a tooth to a predetermined position, in particular an improved position of the tooth, or to monitor the eruption of a tooth, or to monitor the opening or closing of a space between two or more than two teeth, in particular between two adjacent teeth, for example, in order to create a space suitable for fitting a dental implant; and/or detecting or assessing a position or a shape of an orthodontic appliance, in particular an abnormal position or shape of an orthodontic appliance, for example, the detachment of a ring or an orthodontic aligner, and/or an evolution of a position or a shape of an orthodontic appliance and/or a rate of evolution of a position or a shape of an orthodontic appliance, in particular for:

optimizing the date to make an appointment with an orthodontist or a dentist; and/or assessing the effectiveness of an active orthodontic treatment; and/or measuring the activity of an active orthodontic appliance; and/or measuring a loss of effectiveness of a passive orthodontic appliance; and/or dentistry; and/or measuring an evolution of the shape of the teeth of the patient between two dates, for example, during pre-treatment, in particular between two dates separated by an event likely to have changed the position and/or the shape of at least one tooth, for example, separated by the occurrence of an impact on the teeth or by the use of a dental device capable of producing an unwanted effect, for example, intended for treating sleep apnea, or by the occurrence of a graft in the mouth of the patient, in particular a periodontal graft, and in particular a gum graft.

When the static information is used to assess an evolution, it can be compared with a defined situation, at an instant prior to the updated instant, without having recourse to a method according to the invention. For example, when the static information is used to assess an evolution of a position or a shape of a tooth, it can be compared with a position or a shape of this predefined tooth without implementing steps a) to c), with said position or shape being predefined, for example, at the beginning of the treatment or at an intermediate instant of the treatment.

Multiple Execution at Different Updated Instants: Amounts of Movement

An analysis method according to the invention also can be implemented, one or more times, at different "anterior" and "posterior" updated instants, as illustrated in FIG. 3.

Comparing the "anterior" updated spatial information (or the static information) obtained at the anterior updated instant with the "posterior" updated spatial information (or with the static information, respectively) obtained at the posterior updated instant allows an evolution to be determined between these two updated instants. This evolution, which is brought to the time interval between these two updated instants, allows a rate of this evolution to be determined.

The term "amount of movement" refers to the information resulting directly from such a comparison.

The amount of movement particularly can be a movement of a noteworthy point between the two updated instants or, by dividing this movement by the time interval between these two updated instants, an average rate of movement between these updated instants.

The invention thus relates to a method for determining an amount of movement of a dental body of an updated patient comprising steps 1) to 3), and optionally step 4).

In step 1), an analysis method according to the invention is implemented, at the anterior updated instant, so as to obtain the anterior spatial information relating to the updated dental body.

The anterior updated instant can be, for example, less than 3 months, less than 2 months, less than 1 month, less than one week, less than 2 days after fitting an active or passive orthodontic appliance, for example, an orthodontic aligner, an orthodontic arch or a retainer.

The analysis method according to the invention can be implemented several times, as described above, as a function of the desired anterior static information.

In step 2), the same analysis method according to the invention is implemented, at the posterior updated instant, so as to obtain the posterior spatial information. The posterior spatial information therefore relates to the same updated dental body and to the same spatial attribute as the analysis method implemented at the anterior instant.

The posterior updated instant is preferably later than the anterior updated instant bye more than 2 weeks, 1 month, 2 months or 6 months and/or less than 5 years, 3 years or 1 year.

In step the same neural network(s) is used as in step 1). Therefore, step a) is not necessary.

If the analysis method according to the invention has been implemented several times in step 1), the same is the case in step 2), so as to obtain a posterior item of static information comparable to the anterior static information.

In step 3), the anterior and posterior spatial information is compared in order to determine an amount of movement.

The anterior and posterior spatial information are values that can be compared with one another, for example, in terms of a difference.

For example, if the anterior and posterior spatial information is made up of the coordinates $(x_1, y_1$ and $z_1)$ and $(x_2, y_2$ and $z_2)$ of the barycenter of a tooth, at the anterior $t_1$ and posterior $t_2$ updated instants, respectively, in a fixed reference frame relative to the dental arcade, the square root of $(x_2-x_1)^2+(y_2-y_1)^2+(z_2-z_1)^2$ allows the distance covered by this barycenter to be assessed between the anterior $t_1$ and posterior $t_2$ updated instants.

The result of the comparison can be made up of one or more value(s). For example, considering the situation in which the spatial attribute is $(x'; y'; z'; x''; y''; z'')$, with $(x'; y'; z')$ and $(x''; y''; z'')$ being the positions of two noteworthy points P' and P'', respectively, of a tooth in a three-dimensional reference frame, for example, an orthonormal reference frame, $(Ox; Oy; Oz)$, with the origin being, for example, at the center of the dental arcade supporting this tooth. If the anterior and posterior spatial information is denoted $(x_1'; y_1'; z_1'; x_1''; y_1''; z_1'')$ and $(x_2'; y_2'; z_2'; x_2''; y_2''; z_2'')$, respectively, then:

$x_1'$, $y_1'$, $z_1'$ are the values of the coordinates x, y and z, for example, in mm, of point P' at the anterior updated instant;

$x_2'$, $y_2'$, $z_2'$ are the values of the coordinates x, y and z, for example, in mm, of point P'' at the posterior updated instant;

$x_1''$, $y_1''$, $z_1''$ are the values of the coordinates x, y and z, for example, in mm, of point P''' at the anterior updated instant; and $x_2''$, $y_2''$, $z_2''$ are the values of the x, y and z coordinates, for example, in mm, of point P'' at the posterior updated instant.

The result of the comparison then can be made up of the distances covered, between the anterior $t_1$ and posterior $t_2$ updated instants, by point P' and by point P''', for example, as determined above (two values for the result of the comparison), or can be the arithmetic mean of these two distances (one value for the result of the comparison).

In step 4), preferably, said amount of movement is present, for example, on a screen of a personal computer or of a mobile phone of the updated patient and/or of a dental care professional.

As illustrated in FIG. 4, steps 1) and 2) can be implemented several times, by modifying the updated dental body and/or the spatial attribute of the analysis method each time. For example, they each can be repeated for a plurality of teeth of the updated patient. In step 3), the updated anterior and posterior spatial information obtained for each pair of steps 1) and 2) can be compared. The updated anterior and posterior spatial information obtained for different pairs of steps 1) and 2) also can be combined in order to obtain improved information.

The term "dynamic formation" generally refers to all the information resulting directly or indirectly from the implementation, once or several times, of steps 1) to 3), each time at the anterior updated instant $t_1$ and at the posterior $t_2$ updated instant.

Use of Dynamic Information

The dynamic information can be used to assess an evolution of the dental situation of the updated patient.

It can be used to assess whether a rate of movement, by translation or by rotation, of a noteworthy point of the updated dental body is within a range of values defining a set of predefined rates, for example, a set of rates that are considered to be acceptable.

The dynamic information can be used to assess whether the dynamics of an active orthodontic treatment complies with the anticipated dynamics, i.e., if the teeth move at a rate that is in accordance with the orthodontic treatment.

The limits of the acceptability ranges defined for dynamic information, or "dynamic constraints", are preferably defined by a dental care professional.

The dynamic information can be presented in the form a graph.

For example, the dynamic information can be presented on a computer screen or a mobile phone screen.

Preferably, the graph summarizes all the information resulting directly or indirectly from the implementation, once or several times, of steps 1) to 3), each time at the anterior updated instant $t_1$ and at the posterior $t_2$ updated instant.

For example, in FIG. 8, the teeth will be colored as a function of a conformity index that expresses the conformity of the rate of movement of each tooth at a predefined rate, for example, in the context of an orthodontic treatment undergone by the updated patient.

The use of the dynamic information is generally simpler than that of the static information. For example, it is generally easier to determine whether a noteworthy point of a tooth has moved abnormally than to determine whether a position of this point in space is abnormal.

For example, in order to detect relapse, the dynamic constraints can correspond to an authorized movement margin for the barycenter of a tooth. In order to monitor an orthodontic treatment, the dynamic stresses can correspond to a course of movement of one tooth relative to another (reduction or increase in the distance between these teeth), in order to check that the two teeth move toward or away from each other. The dynamic constraints can also correspond to a threshold value for a rate of movement of an orthodontic appliance or a point of a tooth on which the orthodontic appliance acts, to check the activity of the orthodontic appliance.

The dynamic information also can be used to measure an evolution of the shape of a tooth or of a set of teeth.

The dynamic information thus can be particularly used for:

detecting or assessing an evolution of a position or a shape of a tooth and/or a rate of evolution of a position or a shape of a tooth, in particular:

during a pre-treatment period, i.e., in a period that precedes an orthodontic treatment;

in the absence of any orthodontic treatment, in particular to monitor the eruption of a tooth or to detect a relapse or an abnormal position of a tooth or to detect an abrasion of a tooth, for example, due to bruxism, or to monitor the opening or closing of a space between two or more than two teeth, in particular between two adjacent teeth, or to monitor the stability or the modification of the occlusion;

in the context of an orthodontic treatment, in particular to monitor the movement of a tooth to a predetermined position, in particular an improved position of the tooth, or to monitor the eruption of a tooth, or to monitor the opening or closing of a space between two or more than two teeth, in particular between two adjacent teeth, for example, in order to create a space suitable for fitting a dental implant; and/or detecting or assessing an evolution of a position or a shape of an orthodontic appliance and/or a rate of evolution of a position or a shape of an orthodontic appliance, in particular an abnormal position or shape of an orthodontic appliance, for example, the detachment of a ring or an orthodontic aligner, in particular for:

optimizing the date to make an appointment with an orthodontist or a dentist; and/or assessing the effectiveness of an active orthodontic treatment; and/or measuring the activity of an active orthodontic appliance; and/or measuring a loss of effectiveness of a passive orthodontic appliance; and/or dentistry; and/or measuring an evolution of the shape of the teeth of the patient between two dates, for example, during pre-treatment, in particular between two dates separated by an event likely to have changed the position and/or the shape of at least one tooth, for example, separated by the occurrence of an impact on the teeth or by the use of a dental device capable of producing an unwanted effect, for example, intended for treating sleep apnea, or by the occurrence of a graft in the mouth of the patient, in particular a periodontal graft, and in particular a gum graft.

A message can be sent to the updated patient and/or to a dental care professional in order to notify them, particularly when a dynamic constraint is not respected, for example, if an amplitude and/or a rate and/or a direction of a movement of a noteworthy point of a tooth determined from the dynamic information is not (or are not) acceptable.

In one embodiment, the static information and/or the dynamic information are used to assess whether an objective is reached and/or to measure the difference between the dental situation of the updated patient at the updated instant and the achievement of the objective.

The objective is preferably selected from among the following objectives:

the updated patient achieves a Class 1 occlusion for the canines;

the updated patient achieves a Class 1 occlusion for the molars;

the spaces of the anterior sector of the updated patient are closed;

the space resulting from the extraction of a tooth of the updated patient is closed;

the updated patient has a normal horizontal overhang, or "overjet", preferably ranging between 1 and 3 mm;

the updated patient has a normal vertical overhang, or "overbite", preferably ranging between 1 and 3 mm;

the inter-incisal sectors of the upper and lower arcades of the updated patient are not offset;

the updated patient does not have a lateral offset of the lower arcade and/or of the upper arcade relative to a sagittal plane of the head of the patient;

the updated patient does not have a lateral offset of the upper arcade relative to the lower arcade;

an orthodontic appliance, for example, an orthodontic arch and/or an orthodontic aligner and/or the auxiliary appliances, worn by the updated patient is passive, race, no longer modifies the positions of the teeth of the updated patient;

none or limited movements of the teeth of the updated patient are detected during the last two checks of the upper and/or lower arcade, preferably no movement of a tooth of the updated patient has been detected;

all the primary teeth of the updated patient have fallen out;

absence of lateral open bite (closure of the lateral open bite);

absence of posterior open bite;

absence) anterior open bite;

absence of anterior reverse articulation;

absence of posterior reverse articulation;

improvement of crowding;

stabilization of recessions;

closed diastema;

absence of irregularities of the mucosa.

EXAMPLE

In one example, the considered dental body is a pair of two teeth with a determined type or number, for example, the number 13 tooth (right upper canine) and the adjacent number 14 tooth (first right upper premolar). The spatial attribute is a triplet of coordinates, or "parameters", (X, Y, Z) for a vector joining the barycenter of the number 13 tooth and the barycenter of the number 14 tooth. Spatial information is therefore formed by a triplet of values for these coordinates.

The spatial information is measured relative to an orthonormal reference frame (Ox; Oy; Oz), the origin O of which is at the center of the upper denial arcade of the considered patient.

In step A), a historical learning database comprising 100,000 historic records is created.

The historical images are all extra-oral photos, in true colors, taken without a retractor, and then cropped.

The photos have most often been taken with a personal camera, generally a mobile phone, and sometimes with a camera of a dental care professional. They were taken at variable distances from the historical patient, then preferably cropped so that the size of the number 13 and number 14 teeth is substantially the same irrespective of the considered historical image.

Any historical record comprises a set of four historical images of a historical patient that depict all the number 13 and number 14 teeth of the historical patient, and the angulations of which are, respectively, the "front view", "top view", "right view" and "right front view" (in the occlusal plane).

The historical spatial information of a historical record is made up of a vector (Xi, Yi, Zi). In other words, from the barycenter of the number 13 tooth, a movement by a value Xi along the axis Ox, then by a value Yi along the axis Oy, then by a value Zi along the axis Oz leads to the barycenter of the number 14 tooth. The historical spatial information of each record is determined manually, from a three-dimensional model of the dental arcades of the historical patient produced with a 3D scanner.

In step B), a neural network CNN, for example, Google-Net (2015), is trained with the historical learning database so that it is capable of determining a vector between the barycenters of the number 13 and number 14 teeth on the basis of a set of updated images similar to the sets of historical images used for the training.

In step b), an updated patient is considered, for example, a person not scheduled for any orthodontic treatment and not wearing a retainer, at an anterior updated instant $t_1$. They have a mobile phone, to which they have downloaded an application capable of implementing steps b) and c). They wish to check the dental situation relating to their number 13 and number 14 teeth and they launch this application.

The application activates the camera of the mobile phone and guides the updated patient so that they acquire four photos depicting these two teeth at said "front view", "top view", "right view" and "right front view" angulations.

The application then crops these photos, taken at variable distances from the updated patient, so that the size of the number 13 and 14 teeth is substantially the same irrespective of the updated image, and substantially identical to that of these teeth on the historical images.

The application then enters all four updated images into the trained neural network. This trained neural network can be integrated into the application or can be on a computer remote from the mobile phone, in which case the mobile phone sends the four updated images to the remote computer so that it enters them into the trained neural network.

In step c), on the basis of these four updated images alone, the trained neural network provides, preferably in less than 120 sec, 60 sec, 40 sec, 20 sec, 10 sec or 5 sec, an updated item of spatial information. The updated item of spatial information is a vector (Xa, Ya, Za), which in the orthonormal reference frame (Ox; Oy; Oz), the origin O of which is at the center of the upper dental arcade of the updated patient, allows the barycenter of the number 13 tooth of the updated patient to be connected to the barycenter of their number 14 tooth.

The vector (Xa, Ya, Za) is a static item of information that can be compared with predefined static constraints. For example, it is possible to check whether $|Xa|<Sx$, $|$and/or whether $|Ya|<Sy$, and/or whether $|Za|<Sz$, Sx, Sy and Sz are threshold values, for example, 0.5 mm, 0.7 mm and 0.3 mm. It is also possible to check, for example, whether $|Xa|+|Ya|+|Za|<S$, S are a threshold value. If a constraint is not respected, for example, because $|Xa|>Sx$, a message is sent to the updated patient in order to notify them. For example, a message is displayed on their mobile phone screen to ask them to contact a dental care professional.

If the neural network is in a remote computer, the computer transmits the updated spatial information and/or said message to the application.

The updated patient can perform the same steps (activation of the application, taking photos and entering them into the trained neural network) at an anterior updated instant $t_2$, for example, one month after the anterior updated instant.

For this second implementation of the invention, the application can not only analyze the static information obtained at the posterior updated instant, namely a vector (Xa', Ya', Za'), as at the anterior updated instant, but also compare it with the static information obtained at the anterior updated instant, i.e., to the vector (Xa, Ya, Za). It can determine, for example, the following amounts of movement: $|Xa'-Xa|$, $|Ya'-Ya|$, $|Za'-Za|$, $|Xa'-Xa|+|Ya'-Ya|+|Za'-Za|$, $|Xa'-Xa|/(t_2-t_1)$, $|Ya'-Ya|/(t_2-t_1)$, $|Za'-Za|/(t_2-t_1)$, or $(|Xa'-Xa|+|Ya'-Ya|+|Za'-Za|)/(t_2-t_1)$.

These amounts of movement form dynamic information that advantageously teaches the evolution over time of the dental situation relative to the number 13 and 14 teeth, and, more specifically, the relative movement of the number 13 tooth relative to the number 14 tooth. They therefore supplement the static information.

The dynamic information can be compared with predefined dynamic constraints. For example, it is possible to check whether $|Xa'-Xa|/(t_2-t_1)<Vx$, $|Ya'-Ya|/(t_2-t_1)<Vy$, $|Za'-Za|/(t_2-t_1)<Vz$, or whether $(|Xa'-Xa|+|Ya'-Ya|+|Za'-Za|)/(t_2-t_1)<V$, with Vx, Vy, Vz and V being threshold values, for example, of 0.1 mm/month, 0.2 mm/month, 0.1 mm/month and 0.3 mm/month, respectively. If a constraint is not respected, a message is sent to the updated patient in order to notify them. For example, a message is displayed on their mobile phone screen to ask them to contact a dental care professional.

If the neural network is in a remote computer, the computer transmits the updated spatial information and/or all or some of the dynamic information and/or said message to the application.

Preferably, the updated patient implements the operations described above for all the pairs of teeth of their dental arcades (teeth number 1 and number 2, teeth number 2 and number 3, etc.). For each pair of teeth, the application preferably implements a specialized procedure for providing enough photos taken at the different angulations predefined for the considered pair of teeth. The photos for a determined pair of teeth are entered into a neural network specialized for this pair of teeth.

In one embodiment, the dynamic information is used to measure the effectiveness, or "activity", of an active orthodontic appliance, i.e., its ability to act on the dental arcade at the updated instant. For example, the rates of movement of the teeth can be used to determine whether the orthodontic appliance continues to be effective (if these rates are greater than threshold values, for example, at 0.1 min/month) and thus to determine whether the orthodontic appliance must be changed or modified and/or whether an appointment needs to be made with a dental care professional. If appropriate, a written or oral message is sent to the updated patient and/or to the dental care professional.

EXAMPLE

FIG. 6 illustrates an example of the implementation of a method according to the invention. The dates are on the abscissa. The ordinate axis provides the accumulation of the movements in all directions, in millimeters, for all the teeth of the mandibular arcade of a patient.

The solid line curve represents the "actual" evolution. In order to determine this curve, a digital three-dimensional model of the dental arcade of the patient is initially generated with a 3D scanner. It is then deformed in order to correspond to the arrangement of the teeth observed at different instants, by implementing the method described in PCT/EP2015/074859. Each point of this curve requires several hours of computer processing.

The dashed line curve represents the evolution determined according to the invention. Each point of this curve requires only a few seconds of computer processing.

In a highly surprising manner, it can be seen that the dashed line curve follows the solid line curve remarkably well. It therefore realistically represents the actual evolution, even though it is very quick to compute.

As is now clear, the invention provides a solution for determining positions, distances, orientation directions, or orientation courses in the volume of the oral cavity of a patient. This solution is quick, reliable and requires only limited computation resources.

It particularly can be implemented in a few seconds, with an application downloaded onto a mobile phone.

In addition, it provides precise information, with the precision typically being less than 0.3 mm.

Finally, it can be implemented from simple extra-oral photos taken by the patient themselves, with their mobile phone, without particular care and without any 3D model needing to have been generated beforehand.

The invention thus allows the dental situation of any person to be assessed, during an active or passive orthodontic treatment, but also in the absence of any orthodontic treatment, without this person even having previously met a dental care professional.

The invention claimed is:

1. A method for training a neural network intended to analyze a dental situation of an updated patient, said method comprising the following steps:
   A) creating a historical learning database relating to a dental body and to a spatial attribute associated with the dental body;
   the historical learning database comprising more than 1,000 historical records, with each historical record relating to a respective historical patient, comprising:
   a set of historical images all depicting said dental body in said historical patient, called "historical dental body"; and
   an item of spatial information comprising, for the historical patient, a set of values for said spatial attribute, called "historical spatial information";
   B) training the neural network, by providing it with said sets of historical images as input and with said historical spatial information as output, with the spatial attribute defining an ordered sequence of variables in a three-dimensional reference frame.

2. The training method as claimed in claim 1, wherein the neural network is convolutional.

3. The training method as claimed in claim 1, wherein the spatial attribute defines:

a position of one or more noteworthy point(s) of the dental body in a three-dimensional reference frame; and/or one or more vector(s) between noteworthy points of the dental body and/or between a noteworthy point of the dental body and another point.

4. The training method as claimed in claim 1, wherein:

the dental body is a tooth or a set of less than 5 teeth; and/or the spatial attribute comprises less than 30 variables; and/or the set of historical images of any historical record comprises more than two and less than 30 historical images; and/or each historical image of the set of historical images of any historical record has an angulation selected from a group of potential angulations comprising more than 2 and less than 30 potential angulations; and/or at least three historical images of any set of historical images have different angulations.

5. The training method as claimed in claim 1, wherein the historical dental body is a tooth having a predetermined number or a set of teeth comprising a tooth having a predetermined number and one or two teeth adjacent to said tooth.

6. The training method as claimed in claim 1, wherein the historical images are true color photographs, and/or do not depict a dental retractor, and/or are extra-oral.

7. Use of an analysis method as claimed in claim 1 for:

detecting or assessing a position or a shape of a tooth and/or an evolution of a position or a shape of a tooth and/or a rate of evolution of a position or a shape of a tooth; and/or detecting or assessing a position or a shape of an orthodontic appliance and/or an evolution of a position or a shape of an orthodontic appliance and/or a rate of evolution of a position or a shape of an orthodontic appliance; and/or measuring an evolution of the shape of the teeth of the patient between two dates; and/or dentistry.

8. The use according to claim 7, for:

monitoring the eruption of a tooth; and/or detecting a relapse or an abnormal position of a tooth; and/or detecting an abrasion of a tooth; and/or monitoring the opening or closing of a space between two or more teeth; and/or monitoring the stability or the modification of the occlusion;

monitoring the movement of a tooth to a predetermined position; and/or detecting or assessing the detachment of a ring or of an orthodontic aligner;

optimizing the date to make an appointment with an orthodontist or a dentist; and/or assessing the effectiveness of an active orthodontic treatment; and/or measuring the activity of an active orthodontic appliance; and/or measuring a loss of effectiveness of a passive orthodontic appliance; and/or measuring an evolution of the shape of the teeth of the patient between two dates separated by the occurrence of an impact on the teeth or by the use of a dental device intended for treating sleep apnea, or by the occurrence of a graft in the mouth of the patient.

9. A method for analyzing a dental situation of a patient, called "updated patient", at an updated instant, said method comprising the following steps:

analyzing a set of several updated images by means of a neural network so as to obtain an item of spatial information comprising, for the updated patient, a set of values for a spatial attribute, called "updated spatial information", the neural network being trained, before the updated instant, in accordance with a training method comprising the following steps:

A) creating a historical learning database relating to a dental body and to the spatial attribute associated with the dental body;

the historical learning database comprising more than 1,000 historical records, with each historical record relating to a respective historical patient, comprising:

a set of several historical images all depicting said dental body in said historical patient, called "historical dental body"; and an item of spatial information comprising, for the historical patient, a set of values for said spatial attribute, called "historical spatial information"; and B) training neural network, by providing the neural network with said sets of several historical images as input and with said historical spatial information as output, with the spatial attribute defining an ordered sequence of variables in a three-dimensional reference frame;

each image of the set of updated images being acquired by means of an image acquisition device, being compatible with said neural network and depicting said dental body of the updated patient called "updated dental body", the spatial attribute defining:

a position of one or more noteworthy point(s) of the dental body in a three-dimensional reference frame; and/or one or more vector(s) between noteworthy points of the dental body and/or between a noteworthy point of the dental body and another point.

10. The analysis method as claimed in claim 9, wherein the updated images are true color photographs, and/or are extra-oral, and/or the updated patient does not wear a dental retractor.

11. The analysis method as claimed in claim 9, wherein the updated patient wears a dental retractor.

12. The analysis method as claimed in claim 9, wherein:

a plurality of neural networks is trained with respective historical learning databases that differ in that they relate to different dental bodies and/or different spatial attributes, so as to obtain a plurality of specialized neural networks;

updated images are acquired and a set of updated images is generated from said updated images for each of said specialized neural networks;

each of said sets of updated images is analyzed by means of the corresponding specialized neural network, so as to obtain a plurality of updated items of spatial information.

13. The analysis method as claimed in claim 12, wherein each historical learning database relates to a tooth having a number specific to said historical learning database, or a group of teeth, with the numbers of the teeth of said group being specific to said historical learning database.

14. The analysis method as claimed in claim 9, wherein the updated spatial information is used to assess whether an objective is reached and/or to measure the difference between the dental situation of the updated patient at the updated instant and the achievement of the objective, with the objective being selected from among the following objectives:

the updated patient achieves a Class 1 occlusion for the canines;

the updated patient achieves a Class 1 occlusion for the molars;

the spaces of the anterior sector of the updated patient are closed;

the space resulting from the extraction of a tooth of the updated patient is closed;

the updated patient has a normal horizontal overhang;

the updated patient has a normal vertical overhang;

the inter-incisal sectors of the upper and lower arcades of the updated patient are not offset;

the updated patient does not have a lateral offset of the lower arcade and/or of the upper arcade relative to a sagittal plane of the head of the patient;

the updated patient does not have a lateral offset of the upper arcade relative to the lower arcade;

an orthodontic appliance worn by the updated patient no longer acts to modify the positions of the teeth of the updated patient;

no or limited movements of the teeth of the updated patient were detected during the last two checks of the upper and/or lower arcade;

all the primary teeth of the updated patient have fallen out;

absence of lateral open bite;

absence of posterior open bite;

absence of anterior open bite;

absence of anterior reverse articulation;

absence of posterior reverse articulation;

improvement of crowding;

stabilization of recessions;

closed diastema;

absence of irregularities of the mucosa.

15. The analysis method as claimed in claim 9, wherein the image acquisition device is a mobile phone.

16. A method for determining an amount of movement between an "anterior" updated instant and a "posterior" updated instant after the anterior updated instant, said method comprising the following steps:

1) implementing an analysis method as claimed in claim 9, at the anterior updated instant, so as to obtain an anterior updated item of spatial information;

2) implementing an analysis method as claimed in claim 9, at the posterior updated instant, so as to obtain a posterior updated item of spatial information;

3) comparing the anterior and posterior updated spatial information, so as to obtain an amount of movement between the anterior and posterior updated instants;

4) optionally, presenting said amount of movement to the updated patient and/or to a dental care professional.

17. The determination method as claimed in claim 16, wherein the amount of movement defines an amplitude and/or a rate of the movement, by translation and/or by rotation, between the anterior and posterior updated instants, of one or more point(s) of the updated dental body and/or of one or more vector(s) connecting points of the updated dental body or connecting one or more point(s) of the updated dental body and one or more other point(s) of the oral cavity of the updated patient.

18. The determination method as claimed in claim 16, wherein, in step 3), said amount of movement is compared with a threshold value and, depending on the difference between the amount of movement and the threshold value, the following is determined:

an activity index of an orthodontic appliance worn by the updated patient; and/or an index of conformity of the dental situation of the updated patient with a predefined situation by an orthodontic treatment undertaken by the updated patient, or with a situation resulting from an orthodontic treatment undertaken by the updated patient, or, independently of an orthodontic treatment, with a situation defined by a dental care professional.

19. The determination method as claimed in claim 16, wherein the activity index and/or the conformity index are presented in the form of a graph.

20. Use of a determination method as claimed in claim 16 for:

detecting or assessing a position or a shape of a tooth and/or an evolution of a position or a shape of a tooth and/or a rate of evolution of a position or a shape of a tooth; and/or detecting or assessing a position or a shape of an orthodontic appliance and/or an evolution of a position or a shape of an orthodontic appliance and/or a rate of evolution of a position or a shape of an orthodontic appliance; and/or measuring an evolution of the shape of the teeth of the patient between two dates; and/or dentistry.

21. The use according to claim 20, for:

monitoring the eruption of a tooth; and/or detecting a relapse or an abnormal position of a tooth; and/or detecting an abrasion of a tooth; and/or monitoring the opening or closing of a space between two or more teeth; and/or monitoring the stability or the modification of the occlusion;

monitoring the movement of a tooth to a predetermined position; and/or detecting or assessing the detachment of a ring or of an orthodontic aligner;

optimizing the date to make an appointment with an orthodontist or a dentist; and/or assessing the effectiveness of an active orthodontic treatment; and/or measuring the activity of an active orthodontic appliance; and/or measuring a loss of effectiveness of a passive orthodontic appliance; and/or measuring an evolution of the shape of the teeth of the patient between two dates separated by the occurrence of an impact on the teeth or by the use of a dental device intended for treating sleep apnea, or by the occurrence of a graft in the mouth of the patient.

* * * * *